(12) United States Patent
Uchihara et al.

(10) Patent No.: US 7,387,764 B2
(45) Date of Patent: Jun. 17, 2008

(54) CONTAINED OXYGEN ANALYZING APPARATUS AND CONTAINED ANALYZING METHOD

(75) Inventors: Hiroshi Uchihara, Kyoto (JP); Masahiko Ikeda, Kyoto (JP)

(73) Assignee: Horiba, Ltd., Kyoto (JP)

( * ) Notice: Subject to any disclaimer, the term of this patent is extended or adjusted under 35 U.S.C. 154(b) by 719 days.

(21) Appl. No.: 10/446,432

(22) Filed: May 28, 2003

(65) Prior Publication Data

US 2004/0014234 A1    Jan. 22, 2004

(30) Foreign Application Priority Data

May 29, 2002  (JP)  ............................. 2002-155996
Dec. 25, 2002  (JP)  ............................. 2002-373495

(51) Int. Cl.
 *C12Q 1/68*   (2006.01)
 *G01N 31/12*  (2006.01)
 *G01N 7/00*   (2006.01)

(52) U.S. Cl. .............................. 422/80; 422/50; 422/58; 422/68.1; 422/78; 422/83; 422/94; 422/102; 422/103; 422/104; 436/43; 436/127; 436/138; 436/147; 436/155; 436/174; 436/181

(58) Field of Classification Search ................... 422/50, 422/58, 68.1, 78, 80, 83, 94, 102, 103, 104; 436/43, 127, 138, 147, 155, 174, 181; 266/44, 266/101, 200, 249, 265, 271
See application file for complete search history.

(56) References Cited

U.S. PATENT DOCUMENTS 6,552,786 B1    4/2003   Frech et al.

FOREIGN PATENT DOCUMENTS

| JP | 10-73586     | 3/1989  |
| JP | 05-281142    | 10/1993 |
| JP | 10-073586    | 3/1998  |
| JP | 2000-193657  | 7/2000  |

*Primary Examiner*—Brian J Sines

(57) ABSTRACT

An apparatus for analyzing the amount of gas in a solid sample such as a contained oxygen analyzing apparatus and method utilizing a preliminary reducing furnace which can be connected to an analyzing furnace by a transfer unit. A sample such as steel can be reduced in the preliminary reducing furnace and transferred to the analyzing furnace, for example, by a magnetic force, a gripping unit or a transporting sample body holder. A controller can control the application of heat and the mixing of a metal flux to provide discharge gas to an analyzer.

14 Claims, 14 Drawing Sheets

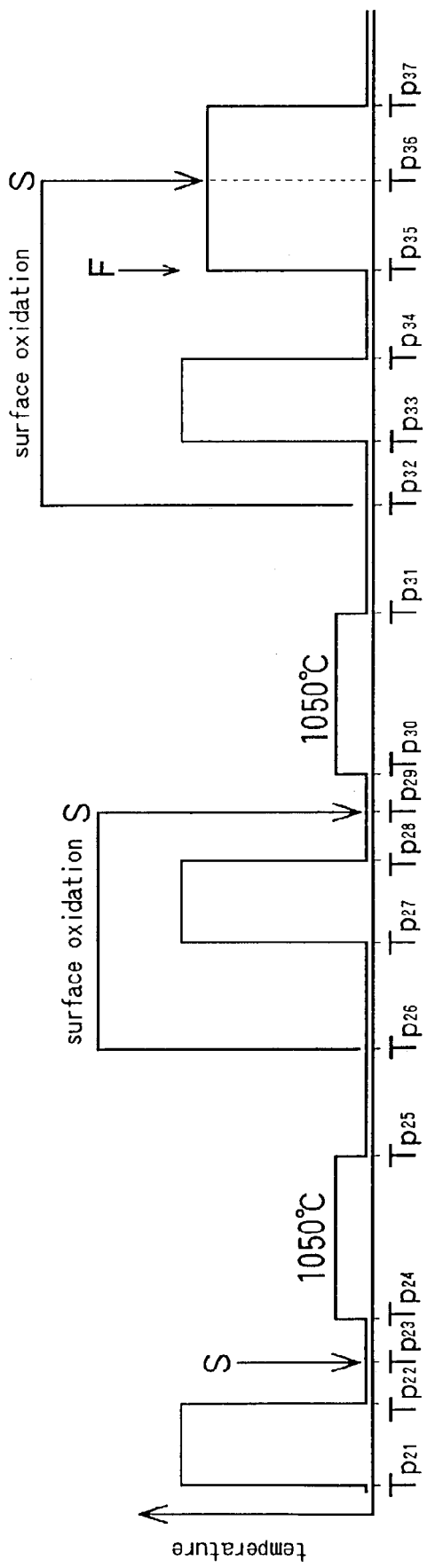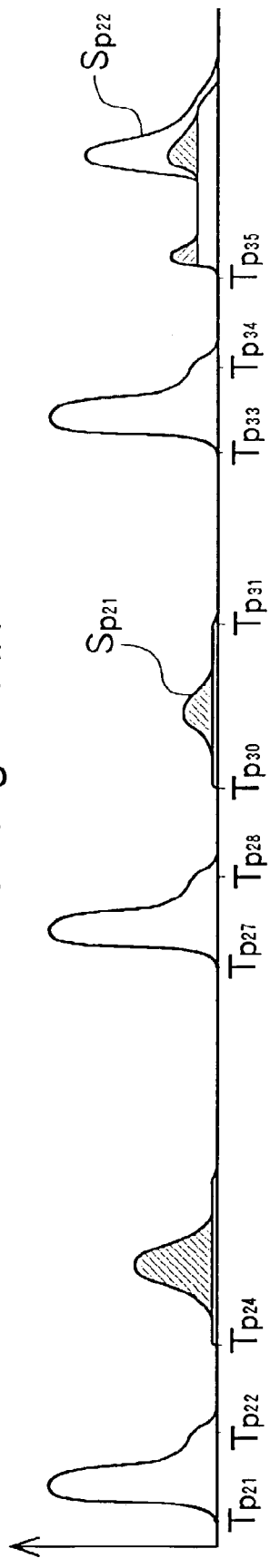
Fig. 14A
Fig. 14B

CONTAINED OXYGEN ANALYZING APPARATUS AND CONTAINED ANALYZING METHOD

BACKGROUND OF THE INVENTION

1. Field of the Invention

The present invention relates to a gas analyzing apparatus, including a contained oxygen analyzing apparatus and a contained oxygen analyzing method which can measure a trace amount of contained oxygen by removing an oxide film on a sample surface to enable a measurement of a small amount of oxygen in a sample to be measured, for example, a metal sample (particularly, steel).

2. Description of Related Art

As a method of quantitatively analyzing an oxygen contained in steel, there has been generally used a method of combining a fusion extraction method in an inert gas, an infrared absorbing method and a thermal conductivity method. The fusion extraction method, the infrared absorbing method and the thermal conductivity method comprise the steps of arranging a graphite crucible in which a sample to be measured is inserted, within a heating furnace, heating and fusing the steel corresponding to the sample to be measured while supplying an inert gas, and analyzing carbon monoxide or carbon dioxide generated at this time, for example, by an infrared gas analyzer.

In order to accurately detect the oxygen contained at only a trace quantity in the sample such as steel, it is necessary to previously remove any oil content, dirt or the like attached to a surface of the sample (hereinafter, refer to as an attachment), and any oxide film. Further, in order to remove any attachment attached to the surface, a preliminary treatment was applied to the sample by heating the sample at 400° C. to 600° C. for about ten minutes.

FIGS. 13a and 13b show one example of a conventionally executed contained oxygen analyzing method. The method of removing the oxide film shown corresponds to a method described in Japanese Unexamined Patent Publication No. 6-148170. FIG. 13A shows the temperature change within a carbon furnace (a graphite crucible) in correspondence to a procedure of contained oxygen analysis, and FIG. 13B shows the change in amount of signals detected by the infrared gas analyzer.

First, the carbon furnace is preliminarily heated at a high temperature, for example, 3000° C. or the like, between time points $Tp_{11}$ and $Tp_{12}$ in FIG. 13A. Next, the surface oxide film is reduced by inputting the sample to be measured into the graphite crucible in which the preliminary heating is finished, at a time point $Tp_{13}$, and heating the sample to be measured to a temperature equal to or less than a melting point (for example, in a range between 900° C. and 1400° C.), between time points $Tp_{14}$ and $Tp_{15}$. Then, an amount of the contained oxygen in the sample to be measured is analyzed by increasing a temperature of the carbon furnace to be equal to or more than 1400° C. (in particular, 2400° C.).

FIGS. 14A and 14B show another example of a contained oxygen analyzing method, in which FIG. 14A shows a temperature change within the carbon furnace in correspondence to a procedure of the contained oxygen analysis, and FIG. 14B shows a change in mount of signals detected by the infrared gas analyzer.

In accordance with the method shown, first, the graphite crucible is preliminarily heated between time points $Tp_{21}$ and $Tp_{22}$, and thereafter, the sample to be measured is input into the graphite crucible at a time point $Tp_{23}$. Next, the surface oxygen is removed by heating the sample to be measured, for example, to 1050° C. in the graphite inert gas between time point $Tp_{24}$ and $Tp_{25}$. Then, the sample to be measured is cooled in the inert gas to be approximately room temperature, and at a time point $Tp_{26}$ the sample to be measured is taken out to the ambient air so as to be oxidized.

Next, the sample to be measured is input into the graphite crucible at a time point $Tp_{29}$, after a preliminary heating is again applied to the graphite crucible between time points $Tp_{27}$ and $Tp_{28}$. The surface oxygen is again removed by heating the sample to be measured, for example, to 1050° C. in the graphite inert gas between time points $Tp_{30}$ and $Tp_{31}$, and the amount of oxidation of the oxide film is measured from a signal amount $Sp_{21}$ at this time. Then, the sample is cooled to approximately room temperature in the inert gas, at a time point $Tp_{32}$ and the sample is taken out to ambient air so as to be again oxidized.

Further, after the preliminary heating is applied for a third time between time points $Tp_{33}$ and $Tp_{34}$, a metal solvent is input into the graphite crucible at a time point $Tp_{35}$, and a metal bath of the metal flux is prepared in the graphite crucible by heating an inner side of the graphite crucible, for example, to 2400° C. Then, a signal amount $Sp_{22}$ of a gas generated by inputting the sample into the graphite crucible is measured at a time point $Tp_{36}$. Accordingly, a contained oxygen amount (a bulk oxygen) of the sample is determined by subtracting the oxygen amount of the oxide film calculated from the signal amount mentioned above from a whole oxygen amount to be calculated ($Sp_{22}-Sp_{21}$).

However, in accordance with the conventional oxygen analyzing method shown in FIGS. 13A and 13B, since the signal $Sp_{11}$ caused by the carbon monoxide gas generated from the graphite crucible is increased at a time of increasing the temperature of the graphite crucible from a preliminary heating temperature between 900 and 1400° C. to 1400° C. or more (in particular, 2400° C.), an influence of fluctuation in the signal $Sp_{11}$ is added to the measured signal amount $Sp_{13}$, so that there is a problem that a magnitude of the signal $Sp_{12}$ caused by the oxygen contained in the sample to be measured cannot be accurately determined.

Especially, since the increase of the signal $Sp_{11}$ caused by the carbon monoxide gas generated from the graphite crucible creates an influence because the oxygen contained in the sample to be measured is only an extremely trace quantity, and it is impossible to measure below 0.5 ppm at the maximum, for example, with respect to an indicated value of 2.9 ppm. That is, in accordance with the conventional oxygen analyzing method shown in FIG. 13, it is impossible to analyze an extremely small quantity of contained oxygen.

Further, in accordance with the conventional oxygen analyzing method shown in FIG. 14, it is necessary to measure the surface oxidation oxygen at two times, so that it is unavoidable to increase the time of measurement. In addition, the subtraction ($Sp_{22}-Sp_{21}$) is executed on the assumption that the amount of the surface oxidation oxygen at the first time is equal to the amount of the surface oxidation oxygen at the second time; however, it is unavoidable that both amounts fluctuate due to the time in contact with the ambient air or the other conditions. That is, in accordance with this example, it is impossible to restrict a dispersion of the surface oxidation to be equal to or less than 0.5 ppm at the maximum with respect to the value of analysis in the case of measuring a trace quantity of contained oxygen of about 2.9 μg/g.

SUMMARY OF THE INVENTION

The present invention takes the above matters into consideration, and an object of the present invention is to provide a contained oxygen analyzing apparatus and a contained oxygen analyzing method which can accurately measure a trace amount of contained oxygen contained in a metal (particularly, a steel) corresponding to a sample to be measured.

In accordance with a first aspect of the present invention, there is provided a contained oxygen analyzing apparatus for analyzing an amount of contained oxygen in a sample to be measured, by inputting both the sample to be measured and a metal flux into a graphite crucible within an analyzing furnace and heating and dissolving them, comprising:

a preliminary reducing furnace which preliminarily reduces an oxide film on a surface of the sample to be measured by heating the sample to be measured to a temperature equal to or less than a melting point in a state of being apart from the ambient air; and a sample inputting means for inputting the sample to be measured into the graphite crucible via a communication passage apart from the ambient air.

Accordingly, by using the contained oxygen analyzing apparatus mentioned above, it is possible to prevent oxide film from being reformed on the surface of the sample to be measured as well as it is possible to completely reduce the oxide film attached to the surface of the sample to be measured, and it is possible to accurately measure the contained oxygen (the bulk oxygen) in the inner portion of the sample to be measured, by dissolving the sample to be measured from which the oxide film is removed.

Further, since the oxide film has been already removed at the time of dissolving the sample to be measured, it is not necessary to carry out a staged heating of the graphite crucible which has been conventionally carried out for removing the oxide film of the sample to be measured, and it is possible to carry out a measurement of the contained oxygen amount in a state in which the inner side of the analyzing furnace is always kept at a fixed temperature. That is, it is possible to completely remove erroneous signals caused by the gas generating from the graphite crucible at a corresponding amount to the temperature as a base line (a reference value), and it is possible to improve an accuracy at that degree.

Since the preliminary reducing furnace is independently provided from the analyzing furnace, it is possible to carry out the preliminary heating of the sample to be measured in parallel to the motion of inputting the metal flux into the graphite crucible and heating and dissolving the metal flux, and to reduce the time required for measurement.

The preliminary reducing furnace can include a preliminary reducing crucible which is arranged in a horizontal direction in such a manner as to be communicated and be connected to an upper portion of the graphite crucible, and a step portion which holds the sample within the crucible by inhibiting the sample within the crucible from moving in the horizontal direction, and the sample inputting means has an actuator which introduces the sample into the analyzing furnace by moving the sample in the horizontal direction against the step portion. In this case, it is possible to transfer the sample from which the surface oxide film is removed into the analyzing furnace from an inner side of the preliminary reducing furnace on the basis of such a simple structure, and to easily and securely inhibit an oxide film from being reformed with respect to the sample, by filling the inner side of the communication passage with an inert gas and evacuating.

In accordance with a second aspect of the present invention, there is provided a contained oxygen analyzing apparatus for analyzing an amount of contained oxygen in a sample, by inputting the sample and a metal flux into a graphite crucible within an analyzing furnace and heating and dissolving them, comprising:

a preliminary reducing furnace which is independently formed from a main body of the oxygen analyzing apparatus;

a sample holding body which is structured such as to be inserted into the preliminary reducing furnace in a state of holding the sample to be measured;

an opening portion which is communicated with the analyzing furnace, is capable of keeping a state of being isolated from the ambient air by circulating the inert gas to the inner portion, is capable of introducing the sample holding body and is provided in a side of the main body of the oxygen analyzing apparatus; and a lid body for the opening portion, wherein the sample holding body has a preliminary reducing crucible having an inflow port for the inert gas in one end side and a discharge port for the inert gas in another end side, and a step portion holding the sample within the crucible in another end side of the crucible, and the sample after being preliminarily reduced is capable of being input into the graphite crucible in a state of being isolated from the ambient air by inserting the sample holding body into the opening portion after heating the sample to a temperature equal to or less than a melting point so as to preliminarily reduce an oxide film on a surface thereof in a state of inserting the sample holding body within the preliminary reducing furnace.

Accordingly, by using the contained oxygen analyzing apparatus mentioned above, it is possible to completely reduce the oxide film attached to the surface of the sample so as to accurately measure only the contained oxygen (the bulk oxygen) in the inner portion of the sample. Further, since the staged heating of the graphite crucible is not carried out, it is possible to measure the trace quantity of contained oxygen while always keeping the inner side of the analyzing furnace at the fixed temperature, and it is possible to improve an accuracy by completely removing the gas generated from the graphite crucible as the base line.

Further, since the preliminary reducing furnace is provided independently from the main body of the contained oxygen analyzing apparatus having the analyzing furnace, it is possible to carry out a preliminary heating of the sample in parallel to the motion of inputting the metal flux into the graphite crucible and heating and dissolving the metal flux, and it is possible to reduce the time required for measurement. Further, since the opening portion is formed in the conventional contained oxygen analyzing apparatus, it is possible to transfer the sample to be measured after the preliminary reducing is applied into the analyzing furnace in a state of being isolated from the ambient air, and it is possible to analyze a trace quantity of contained oxygen.

Since a state isolated from ambient air is formed by the flow of the inert gas, it is possible to securely inhibit the intrusion of the ambient air by the flow (pressure) of the inert gas even when any gap which may form an intrusion path for the ambient air exists in the sample holding body, and it is possible to securely keep sample isolated from the ambient air. That is, the structure of the sample holding body has a size capable of receiving the preliminary reducing crucible and a construction capable of purging by inert gas. Further, since the lid body is formed in the opening portion, it is possible to restrict the gas amount of the inert gas discharged from the opening portion, and it is possible to reduce a running cost at that degree.

The structure may be made such that the apparatus has a lid body capable of opening and closing the discharge port for the inert gas in another end side of the sample holding body from one end side thereof. In this case, it is possible to restrict the amount of inert gas discharged from the sample holding body, and it is possible to reduce cost.

In accordance with a third aspect of the present invention, there is provided a contained oxygen analyzing apparatus for analyzing an amount of contained oxygen in a sample to be measured, by inputting the sample and a metal flux into a graphite crucible within an analyzing furnace and heating and dissolving them, comprising:

a sample take-out unit for temporarily taking out the sample to be measured within the graphite crucible in a state of being isolated from ambient air and holding the sample to be measured, wherein the sample in which an oxide film on a surface thereof is preliminarily reduced by being heated to a temperature equal to or less than a melting point within the graphite crucible is taken out from the graphite crucible by using the sample take-out unit, and only metal flux is input to the graphite crucible and heated and dissolved, and next the sample to be measured is input into the graphite crucible in a state of being isolated from the ambient air, thereby being heated and dissolved, so that the contained oxygen is allowed to be analyzed.

Accordingly, by using the contained oxygen analyzing apparatus mentioned above, it is possible to completely reduce the oxide film attached to the surface of the sample to be measured so as to accurately measure only the contained oxygen (the bulk oxygen) in the inner portion of the sample to be measured. Further, since a staged heating of the graphite crucible is not carried out, it is possible to measure the trace quantity of contained oxygen in a state of always keeping the inner side of the analyzing furnace at a fixed temperature, and it is possible to improve the accuracy by completely removing the gas generated from the graphite crucible as a base line.

Further, it is possible to achieve a simplification and a downsizing of the apparatus structure by carrying out a preliminary heating of the sample to be measured within the analyzing furnace. Further, since a volumetric capacity of a portion forming the state of being isolated from the ambient air is reduced, it is possible to form a state of being isolated from ambient air at a low cost.

The sample to be measured can be a steel sample, and the sample take-out unit has a magnetic force induction portion capable of taking out the steel from the inner side of the graphite crucible due to an attraction of a magnetic force. In this case, it is possible to easily take out the steel from the graphite crucible, and the apparatus structure becomes simple.

The structure may be made such that the sample to be measured is a steel, and the sample take-out unit has a rod body forming a magnetic force application portion at least in a leading end portion thereof and capable of taking-out the steel within the graphite crucible from the inner side of the graphite crucible on the basis of the magnetic force. In this case, it is possible to securely adsorb the steel without greatly strengthening the magnetic force generated from the magnetic force application portion formed in the leading end portion of the rod body, so that an energy saving is achieved and motions of peripheral equipment are not affected at all. Further, since the motion of taking out the steel from the inner side of the graphite crucible on the basis of the magnetic force is sufficiently achieved by a vertical slide of the rod body, it is possible to easily achieve automation.

In this case, the magnetic force application portion can be simplified in structure by being formed by a permanent magnet, and it is possible to reduce the manufacturing cost; however, it is possible to easily achieve an automatic control by setting the magnetic force application portion to an electromagnet.

The structure may be made such that the sample take-out unit has a gripping unit for gripping the sample to be measured by a leading end portion so as to take out the sample to be measured from the inner side of the graphite crucible, a fiber scope for checking a state near the leading end portion by an image, a display portion displaying the image transmitted by the fiber scope, and an operation portion for the gripping unit. In this case, it is possible to analyze the contained oxygen amount without selecting a material of the sample to be measured. Further, since it is possible to operate the operation portion for the gripping unit while viewing the image displayed on the display portion, it is possible to securely grip the sample to be measured in the state of being isolated from the ambient air so as to take it out from the inner side of the graphite crucible, and it is possible to again input into the graphite crucible.

In accordance with a fourth aspect of the present invention, there is provided a contained oxygen analyzing method comprising the steps of:

heating a sample to be measured to a temperature equal to or less than a melting point so as to preliminarily reduce an oxide film on a surface thereof;

inputting a metal flux into a graphite crucible and heating the metal flux to be equal to or more than a melting point thereof and equal to or less than a boiling point;

reducing an oxygen contained in the metal flux by dissolving the metal flux;

determining a gas amount as a reference value in a state in which the gas amount generated from the heated graphite crucible is stable;

inputting the sample to be measured after a preliminary reduction into the graphite crucible, in a state of keeping a temperature of the graphite crucible at this time constant; and analyzing the contained oxygen amount of the sample to be measured from an amount of generated gas increased thereby, wherein all of the steps are carried out within a space communicated in a state of being isolated from the ambient air.

In accordance with a fifth aspect of the present invention, there is provided a contained oxygen analyzing method comprising the steps of:

heating a sample to be measured to a temperature equal to or less than a melting point so as to preliminarily reduce an oxide film on a surface thereof;

inputting a metal flux into a graphite crucible and heating the metal flux to be equal to or more than a melting point thereof and equal to or less than a boiling point;

reducing an oxygen contained in the metal flux by dissolving the metal flux;

determining a gas amount as a reference value in a state in which the gas amount generated from the heated graphite crucible is stable;

inputting the sample to be measured after the preliminary reduction into the graphite crucible, in a state of keeping a temperature of the graphite crucible at this time constant; and analyzing the contained oxygen amount of the sample to be measured from an amount of generated gas increased thereby, wherein all of the steps are carried out in a state of being isolated from the ambient air by a circulation of an inert gas.

In accordance with a sixth aspect of the present invention, there is provided a contained oxygen analyzing method comprising the steps of:

inputting a sample to be measured into a graphite crucible;

heating the sample to be measured to a temperature equal to or less than a melting point so as to preliminarily reduce an oxide film on a surface thereof;

taking out the sample to be measured from the graphite crucible;

heating the graphite crucible into which a metal flux is input to be equal to or more than a melting point thereof and equal to or less than a boiling point;

reducing and dissolving an oxygen contained in the metal flux by dissolving the metal flux;

determining a gas amount as a reference value in a state in which the gas amount generated from the heated graphite crucible is stable;

inputting the sample to be measured after a preliminary reduction into the graphite crucible, in a state of keeping a temperature of the graphite crucible at this time constant; and analyzing the contained oxygen amount of the sample to be measured from an amount of generated gas increased thereby, wherein all of the steps are carried out in a state of being isolated from the ambient air.

That is, since it is possible to input the sample to be measured from which the surface oxide film is removed into the graphite crucible, after previously removing the surface oxide film of the sample, keeping the sample in a state of being isolated from ambient air, and determining the gas amount as a reference value in a state in which the gas amount generated from the graphite crucible dissolving the metal flux becomes stable, it is possible to accurately determine the generation amount of the gas caused by the trace quantity of contained oxygen contained in the inner portion of the sample to be measured by subtracting the reference value from all the measured values.

The present invention further includes a method of analyzing the amount of gas in a solid sample by heating the sample to reduce any film on a surface of the sample. Simultaneously, an analyzing furnace unit can be heated to preliminarily degasify the analyzing furnace unit and to accept the introduction of a metal flux material to form multi-metal flux. The gas output from the metal flux material and the analyzing furnace unit can be monitored until it becomes a constant value, and this value can be stored as a representative signal of the constant value of gas outputting. The reduced sample can be transferred in an inert environment to the analyzing furnace unit so that the reduced sample and the metal flux material can be heated to a molten state whereby the gas is discharged by the molten sample, and the metal flux material can be measured and corrected relative to the stored reference value to determine the amount of gas.

The present invention provides an apparatus for analyzing the amount of gas in a solid sample by providing a reducing furnace for heating the sample to reduce any film such as an oxide film on the surface of the sample and an analyzing furnace unit for melting the sample to provide gases to an analyzer unit. A transfer unit can transfer the sample from the reducing furnace unit to the analyzing furnace unit in an inert environment. A controller can coordinate the applications of temperature, the transfer of the sample, the introduction of a metal flux and the preliminary heating and degassing operation states. The transfer unit can include a movable magnetic member, a communication passage extending between the reducing furnace unit and the analyzing furnace unit, or alternatively, a sample holding body which can hold the sample when it is inserted into the reducing furnace and then can transfer the reduced sample in an inert environment for release into the analyzing furnace unit.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 14 is a view describing another example of the motion of the conventional contained oxygen analyzing apparatus.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Figure 1:
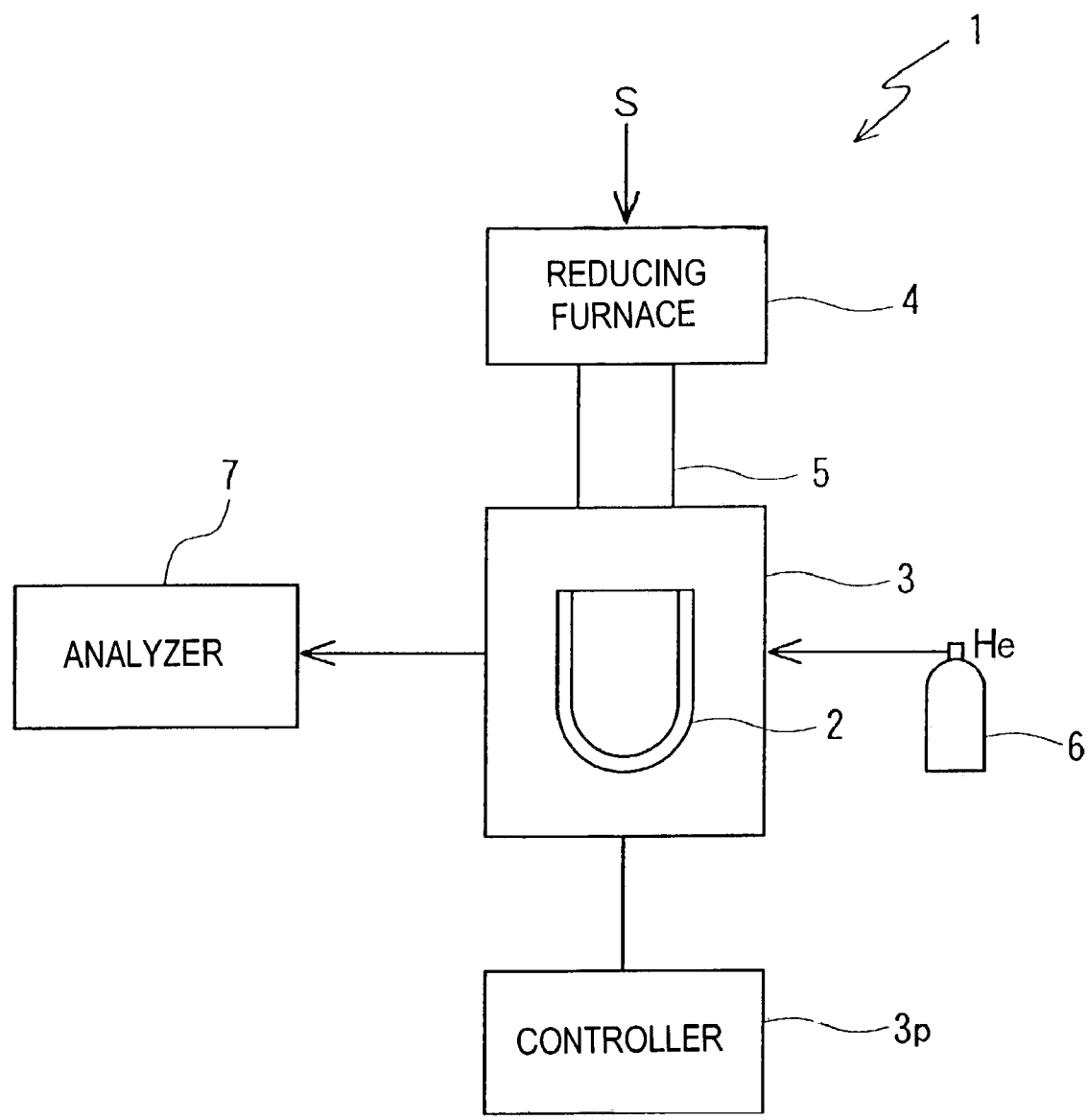
FIG. 1 is a view schematically showing a structure of a main portion of a contained oxygen analyzing apparatus in accordance with a first embodiment.
Figure 2:
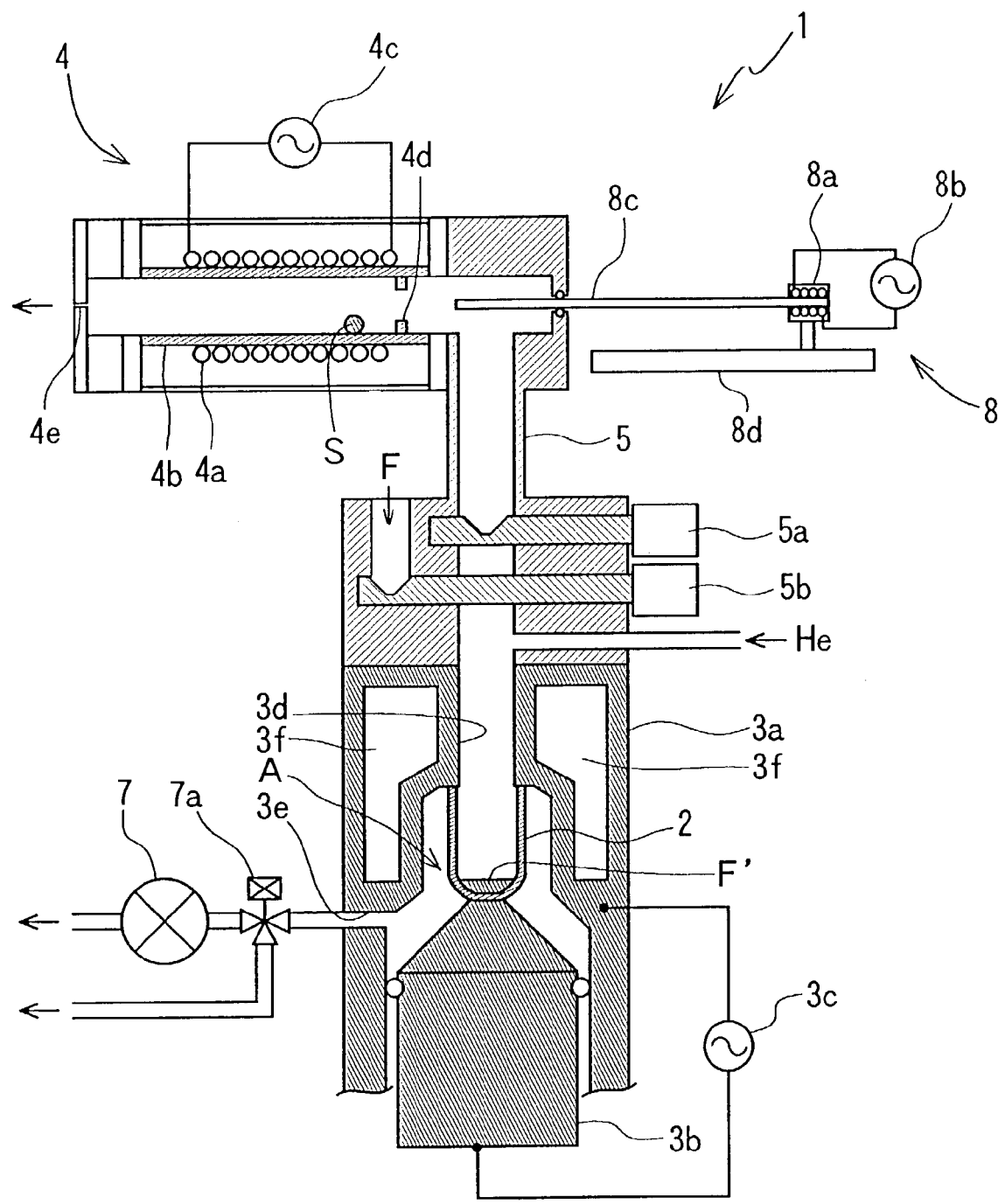
FIG. 2 is a view showing a structure of the contained oxygen analyzing apparatus.
Figure 3:
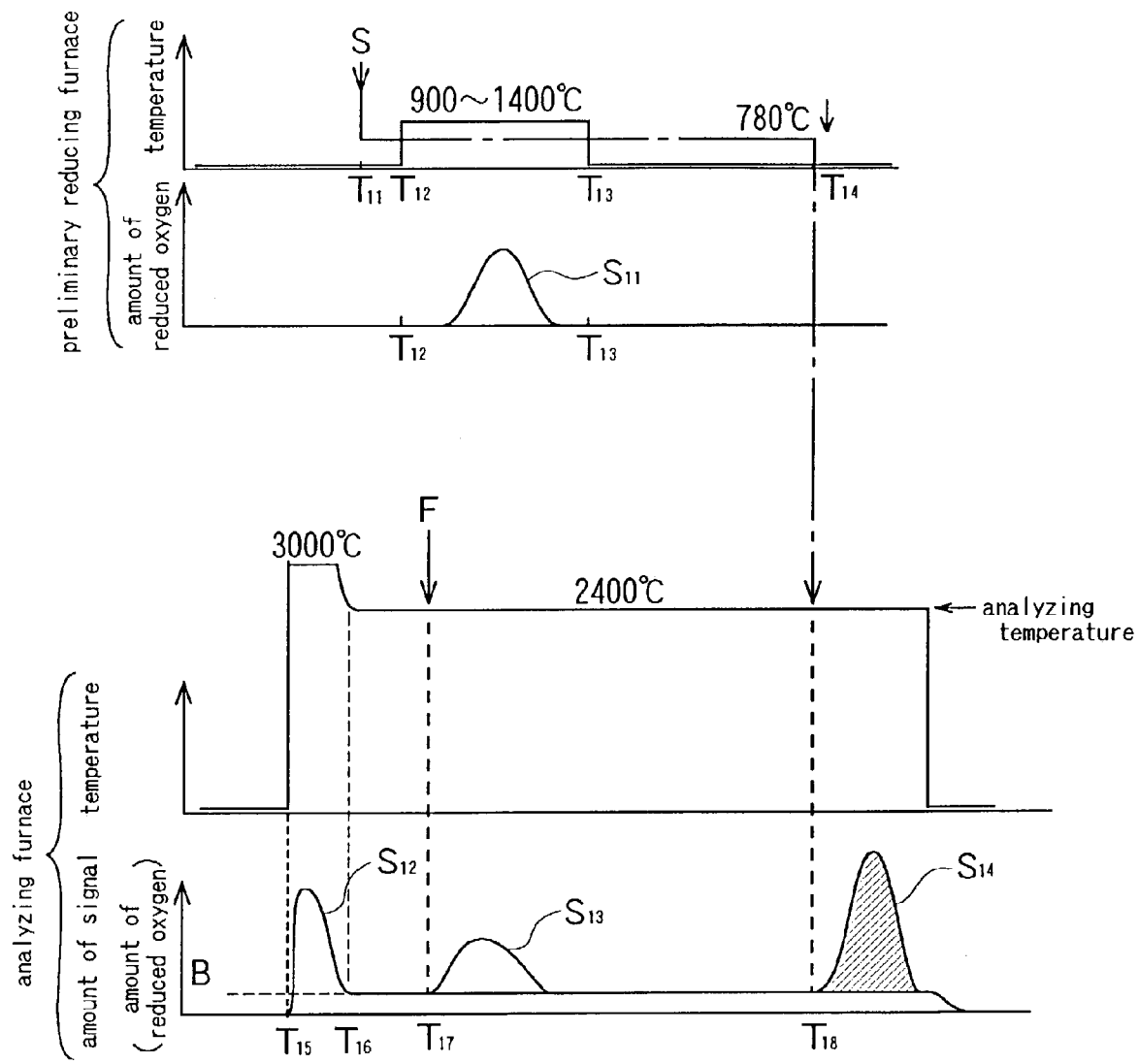
FIG. 3 is a view for describing a motion of the contained oxygen analyzing apparatus.
Figure 4:
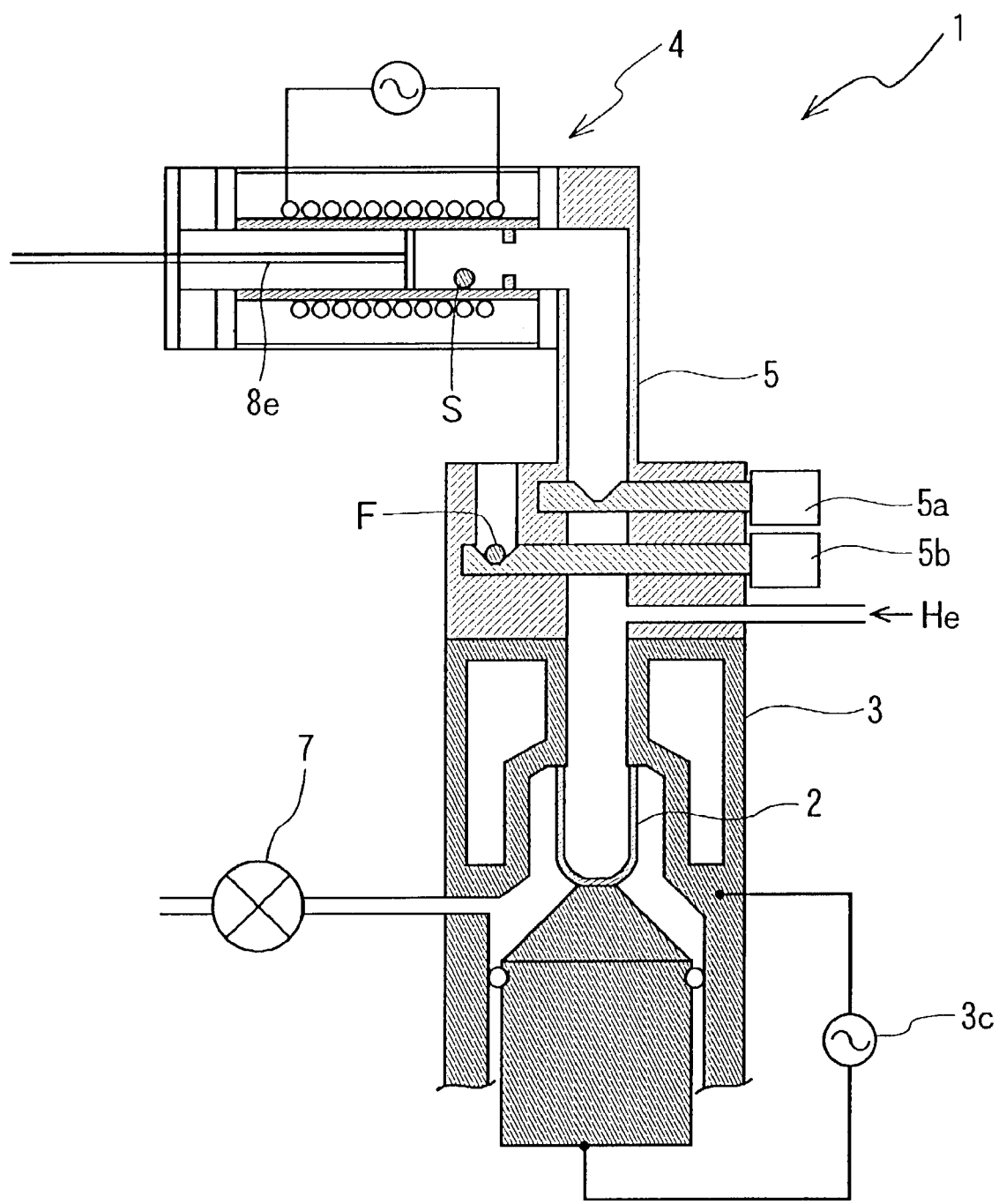
FIG. 4 is a view showing a modified embodiment of the contained oxygen analyzing apparatus.

A description will be given of embodiments in accordance with the present invention with reference to the accompanying drawings. FIGS. 1 to 3 show a structure of a contained oxygen analyzing apparatus 1 in accordance with a first embodiment. A sample S to be measured in the present embodiment is, for example, steel, and a contained oxygen analyzing apparatus 1 in accordance with the present invention is structured such as to measure a trace quantity of oxygen contained in an inner portion of the steel. Further, FIG. 4 is a view showing a modified first embodiment of the embodiment in FIG. 2.

As shown in FIG. 1, the contained oxygen analyzing apparatus 1 has an analyzing furnace 3 which includes a graphite crucible 2 (hereinafter, refer also to as a carbon furnace 2) for inserting the sample S into an inner portion thereof, a preliminary reducing furnace 4 which preliminarily reduces an oxide film on a surface of the sample S by heating the sample S at a temperature equal to or less than a melting point thereof, a communication passage 5 for communicating and connecting the preliminary reducing furnace 4 to the analyzing furnace 3, a gas bomb 6 which supplies an inert gas such as helium (He) or the like to the analyzing furnace 3, and an infrared gas analyzer 7 which measures an amount of generated gas by analyzing the inert gas passing through the analyzing furnace 3. Further, reference symbol 3p denotes a power control portion for the analyzing furnace 3.

FIG. 2 shows detail structure of the contained oxygen analyzing apparatus 1. In FIG. 2, the graphite crucible 2 is a closed-end tubular body having an approximately U-shaped cross section, and is placed within a space A shut off from the ambient air so as to be clamped between an upper electrode 3a and a lower electrode 3b which constitute the analyzing furnace 3. Reference symbol 3c denotes a power source which heats the graphite crucible 2 by applying an electric current controlled by the power control portion or controller 3p to a portion between both of the electrodes 3a and 3b, reference symbol 3d denotes an introduction portion which introduces the sample S to be measured and a metal flux F into an upper portion of the analyzing furnace 3 and introduces the helium gas (He). Reference symbol 3e denotes a discharge portion for the helium gas (He) passing through the graphite crucible 2. As can be appreciated, the controller can include a microprocessor with a stored program to permit an automatic control of different steps of the present procedure.

Reference symbol 3f denotes an inner space of the upper electrode 3a. It is possible to rapidly cool the graphite crucible 2, for example, by circulating a cooling water within the inner space 3f. Further, a flow passage switching valve 7a is formed between the analyzing furnace 3 and the analyzer 7, whereby it is possible to select whether the gas fed from the discharge portion 3e is supplied to the analyzer 7 or the gas is discharged.

The preliminary reducing furnace 4 has an approximately tubular preliminary reducing crucible 4b which is arranged in a horizontal direction, for example, in such a manner as to be between the windings of a heater 4a, a power source 4c for the heater 4a, and a step portion 4d for holding the sample S to be measured within the graphite crucible 4b by inhibiting the sample S from moving in a horizontal direction within the graphite crucible 4b. Further, one end side of the analyzing furnace 3 is communicated and connected to the communication passage 5, and a discharge hole 4e for the helium gas (He) is formed in another end side.

In this case, a heat source for the preliminary reducing furnace 4 is not limited to an electric furnace using the heater 4a, and it is possible to use various types of heat sources such as an impulse furnace, an induction heating furnace or the like. Further, the gas used for the reduction is not limited to helium (He), and other inert gases such as an argon (Ar) or the like may be used. In addition, other gases than an inert gas may be used, for example, a material such as a hydrogen or the like which tends to be combined with an oxygen may be used.

In any case, the sample S to be measured is structured such that an oxide film on a surface layer thereof can be reduced by being heated in a state of being isolated from ambient air.

Reference numeral 8 denotes a sample inputting unit for inputting the sample S to be measured which is positioned within the preliminary reducing furnace 4, into the graphite crucible 2. The sample inputting unit 8 has an electromagnet 8a which attracts the sample S to be measured on the basis of an attracting force using magnetic flux, a power source 8b thereof, a rod body 8c made of a magnetic body for applying a smaller magnetic force to the sample S to be measured, and a slide driving portion 8d which moves the sample S in a horizontal direction against the step portion 4d by moving the rod body 8c in the horizontal direction, in the present embodiment. That is, each of the portions 8a to 8d moves the sample S in the horizontal direction against the step portion 4d, thereby structuring an actuator for introducing the sample S to be measured into the analyzing furnace 3.

In this case, in accordance with the present embodiment, it is possible to electrically control the transfer of the sample S to be measured by using the sample inputting unit 8, by using the electromagnet for the sample inputting unit 8, and it is possible to effectively apply a weak magnetic force to the sample S to be measured by using the rod body 8c of the magnetic body; however, the present invention is not limited to this structure. That is, a permanent magnet may be used for the sample inputting unit 8, and the magnetic force may be directly applied to the sample S to be measured without using the rod body 8c.

Further, in the case that the sample S is not a magnetic body, it is possible to move the sample S to be measured in the horizontal direction against the step portion 4d by pressing it from the other end side of the preliminary reducing furnace 4 by a rod or piston body 8e, as shown by the modified embodiment of FIG. 4. That is, the sample S to be measured in accordance with the present invention is not limited to a magnetic body such as steel or the like, and may be a nonferrous metal such as copper or the like, and in this case, various modifications can be considered for the sample inputting unit 8.

The communication passage 5 has a columnar sample holder 5a for temporarily receiving the sample S to be measured input by the sample inputting unit 8 and thereafter inputting into the graphite crucible 2, and a columnar sample holder 5b for temporarily receiving the metal flux F, for example, tin (Sn) in the same manner and inputting into the graphite crucible 2. In this case, since detailed structures of the sample holders 5a and 5b are as shown in Japanese Unexamined Patent Publication No. 2000-55794 proposed by the inventors of the present application, a detailed description will be omitted.

With regard to the analyzer 7, as an example of a concentration analyzer capable of accurately analyzing a concentration of the oxygen, for example, there can be a non-dispersive infrared gas analyzer (NDIR); however, the kinds thereof is not limited as long as it can accurately analyze the oxygen corresponding to the sample to be measured. For example, a mass spectrometer may be used in place of the NDIR. Further, the structure may be made such as to simultaneously analyze the contained amount of other components than oxygen contained in the sample S to be measured, by using a multi component analyzer such as a Fourier transform infrared gas analyzer (FTIR) or the like.

FIG. 3 is a diagram describing a method of analyzing the oxygen contained in the sample S using the contained oxygen analyzing apparatus 1. An upper half diagram in FIG. 3 shows the motion within the preliminary reducing furnace 4, and a lower half of the diagram shows a motion within the analyzing furnace 3. In both cases, there is shown a change of a temperature within the furnace in accordance with time and a change in an amount of reduced oxygen thereby in accordance with time in a corresponding manner.

In this embodiment, the sample S to be measured is input into the preliminary furnace 4 at a time point $T_{11}$, and the inner side of the preliminary furnace 4 is heated at a temperature equal to or less than a boiling point (1540° C.) of steel, for example, at a temperature between 900 and 1400° C., and a degasification for removing the oxide film on the surface thereof is applied, at a time point $T_{12}$. At this time, the oxygen is reduced from the oxide film on the surface of the sample S to be measured, thereby being converted into a gas such as a carbon monoxide (CO) or the like, as shown by $S_{11}$ and being discharged from the discharge hole 4e.

This preliminary reduction is carried out, for example, for five minutes, and the sample S to be measured is cooled by stopping the heat applied by the heater 4a at a time point $T_{13}$. In this case, since the preliminary reduction, mentioned above, is carried out while supplying helium gas (He), the periphery of the sample S is securely isolated from ambient air on the basis of the circulation of the helium gas (He). In particular, even if the inner side of the communication passage 5 and the preliminary reducing furnace 4 are not completely sealed but have small gaps, the stream of the helium gas (He) is generated from the inner side of the communication passage 5 or the preliminary reducing furnace 4 toward the outer side via the gap, and an inside pressure becomes higher than an outside pressure, so that the ambient air does not move against this greater pressure and flow into the inner side.

Further, magnetism is generated by the electromagnet 8a at a time point $T_{14}$ at which the temperature of the sample S to be measured (steel) is lowered to be equal to or less than the Curie temperature, and the rod body 8c is slid by the slide driving portion 8d. Accordingly, it is possible to move the steel S by using the attractive force generated by the magnetic force so as to move the steel S just above the communication passage 5 over the step portion 4d, and it is possible to input the steel S into the sample holder 5a by stopping the current application to the electromagnet 8a.

On the other hand, within the analyzing furnace 3, the inner side of the analyzing furnace 3 is heated, for example, up close to 3000° C. and the oxygen therein is degasified, at a time point $T_{15}$, and a temperature within the analyzing furnace 3 is controlled to an analyzing temperature (for example, 2400° C.) at a time point $T_{16}$. The carbon monoxide (CO) generated within the analyzing furnace 3 is temporarily increased and again reduced as shown by a curve $S_{12}$. In this case, the gas (CO) is generated in a steady manner from the graphite crucible 2 after being degasified, even in the state of being controlled to the analyzing temperature.

Next, when inputting tin, Sn, corresponding to the powder or granular metal flux F into the graphite crucible 2 by using the sample holder 5b at a time point $T_{17}$, the tin Sn is dissolved in correspondence thereto, and the oxygen in the flux F is discharged, whereby the carbon monoxide (CO) is generated.

In this case, reference symbol $S_{13}$ denotes an amount of the carbon monoxide (CO) generated by inputting the tin Sn. It is possible to securely dissolve the heat oxide by using the metal flux F as shown in the present embodiment, and it is possible to prevent the generated carbon monoxide (CO) from being collected.

Further, when the inner side of the analyzing furnace 3 is made stable at the analyzing temperature, the oxygen in the flux F is finally all discharged, and the concentration of the carbon monoxide (CO) detected by the analyzer 7 is stable. Then, the metal flux F of the dissolved tin Sn (refer to FIG. 2) is formed within the graphite crucible 2.

In this case, the degasification of the graphite crucible 2 within the analyzing furnace 3 and the formation of the metal flux F' by the tin Sn may be simultaneously carried out in parallel to the reduction of the oxide film of the sample S to be measured within the preliminary reducing furnace 4, whereby it is possible to shorten the measuring time.

Next, in a stage in which the concentration of the carbon monoxide (CO) is stable, the concentration of the carbon monoxide (CO) detected at this time is stored as a reference value (a base line) B for measurement, and the sample S to be measured after being preliminarily reduced is input into the graphite crucible 2 by using the sample holder 5a at a time point $T_{18}$, in a state in which the temperature of the graphite crucible 2 is make stable at the analyzing temperature. Reference symbol $S_{14}$ denotes an amount of the carbon monoxide (CO) generated in accordance with the input of the sample S to be measured.

Further, it is possible to accurately determine the amount of the oxygen contained in the sample S to be measured, by integrating the measured value in an upper part (an increased part) from the base line B. Since the surface oxidization of the sample to be measured is 0.3 μg/g and an analysis target level is about 3 μg/g, an influence of a dispersion in measurement is great if the oxygen contained in the oxide film is added to the result of analysis, so that the formula R=0.5 is established; however, since the present invention can measure by completely removing the surface oxide film, it is possible to improve the accuracy of the analysis.

In this case, on the assumption that the whole weight of the sample S to be measured is 1 g, the weight of the oxide film is extremely small, for example, about 150 nm. That is, it is 0.000015/3.15 with respect to the sample having a radius 3.15 mm, and can be disregarded with respect to the whole weight. In other words, in a state in which the concentration of the oxide film is rich, the oxide is $$3 \mu g/(5.1 \times \pi \times \tfrac{1}{3} \times 0.0004465 \times 1000\ \mu g) = 0.3/9.54 = 0.03,$$
and $$O_2/Fe_2O_3 = 32/(55.8 \times 2 + 16 \times 3) = 0.2.$$

Accordingly, since an average concentration of $Fe_2O_3$ contained in the thin film of 150 nm is 0.2×15%=0.03, the accuracy of analysis is R=0.1 with respect to a value of analysis 3 μg/g, and accordingly is improved.

In accordance with the present invention, since a differential time is provided between the input of the metal flux F and the input of the sample S to be measured, it is possible to heat at the fixed analyzing temperature until the oxygen contained in the metal flux F' and the carbon monoxide (CO) generated in the steady manner from the graphite crucible 2 are stable, and input the sample S to be measured after setting them at the stable time point to the base line B, so that it is possible to securely correct the base line B. Accordingly, it is possible to dramatically improve the accuracy of analysis. In addition, in accordance with the present invention, since the surface oxide film is removed only one time, the measurement can be rapidly carried out in comparison with the prior art shown in FIG. 14.

Figure 5A:
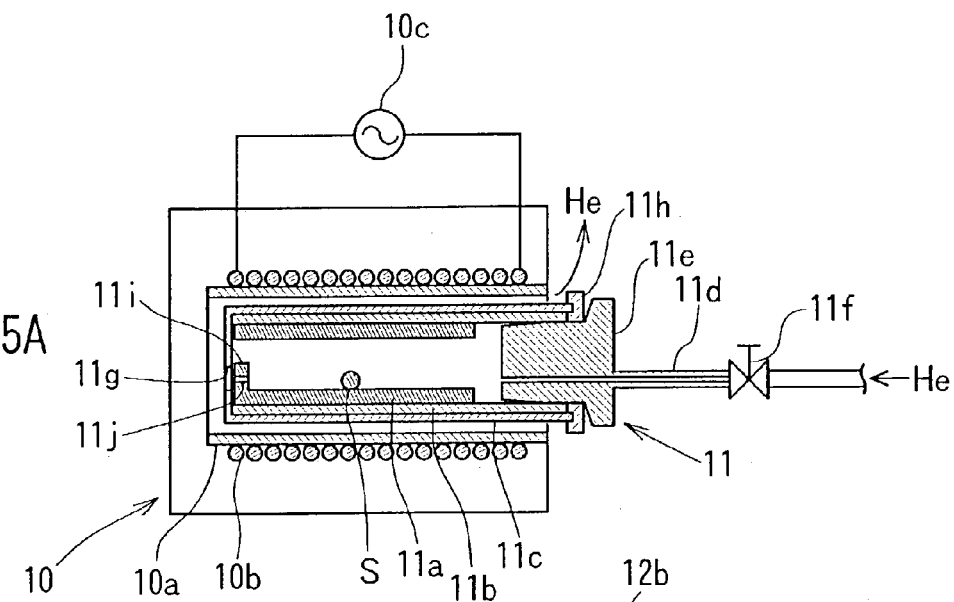
FIG. 5 is a view showing a structure of a contained oxygen analyzing apparatus in accordance with a second embodiment.
Figure 5B:
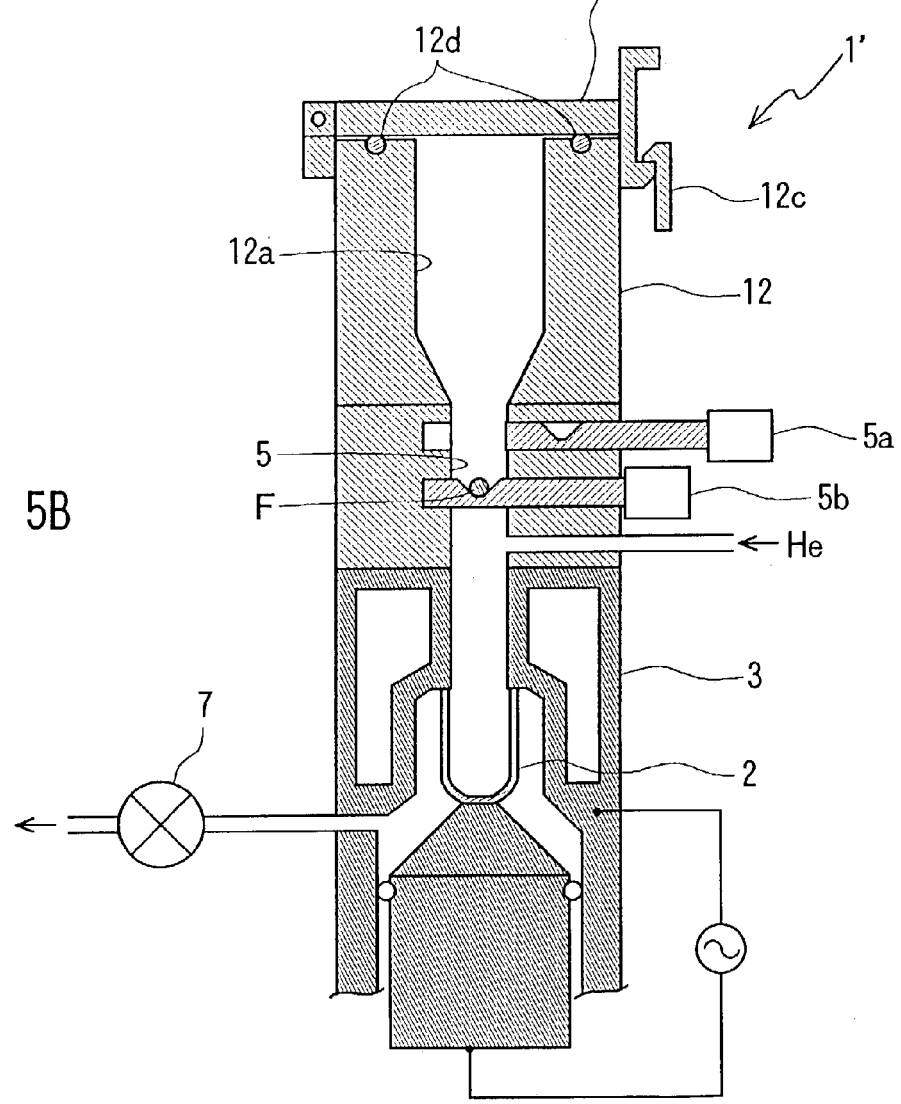
Figure 6:
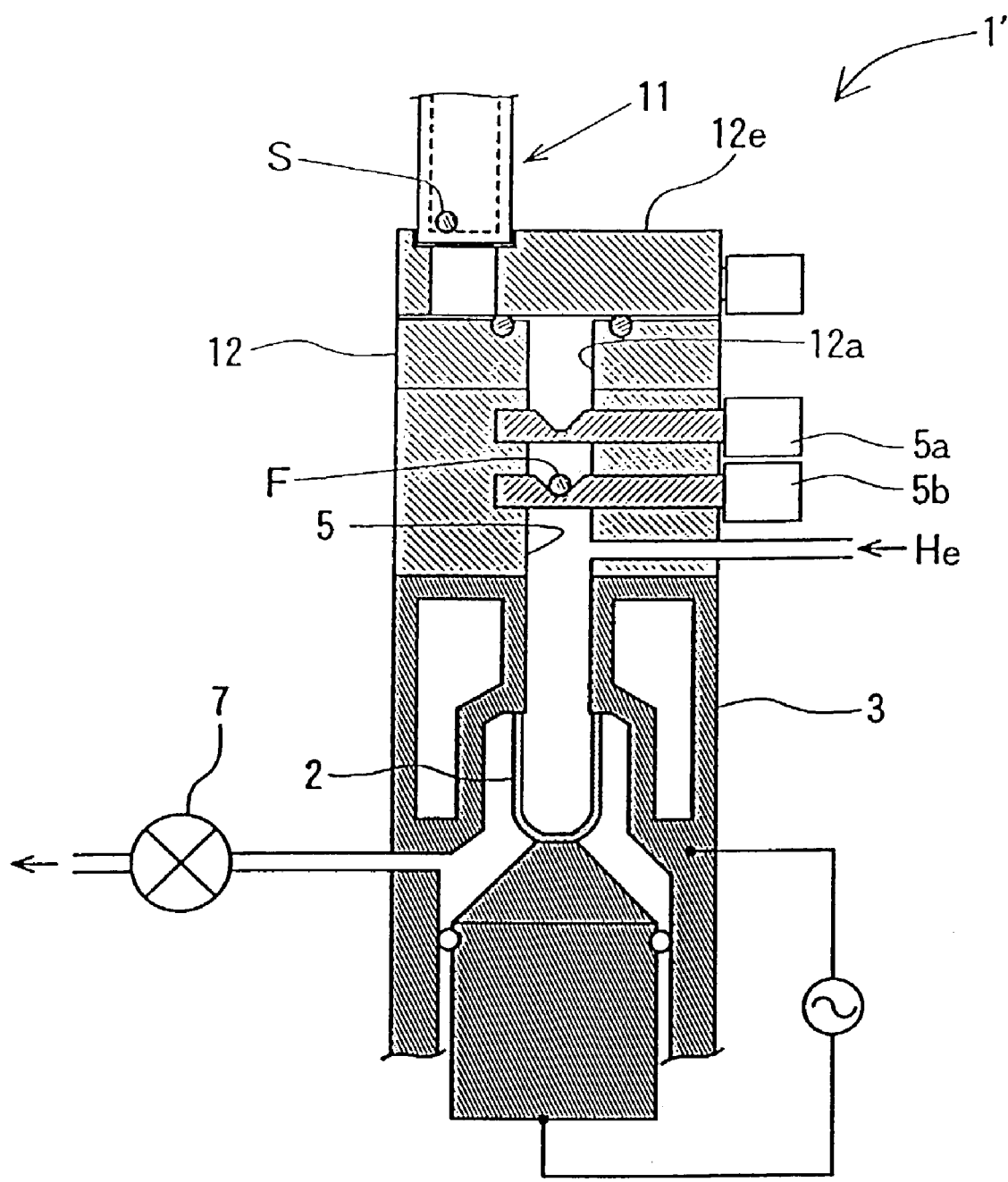
FIG. 6 is a view showing a modified embodiment of the contained oxygen analyzing apparatus.
Figure 7:
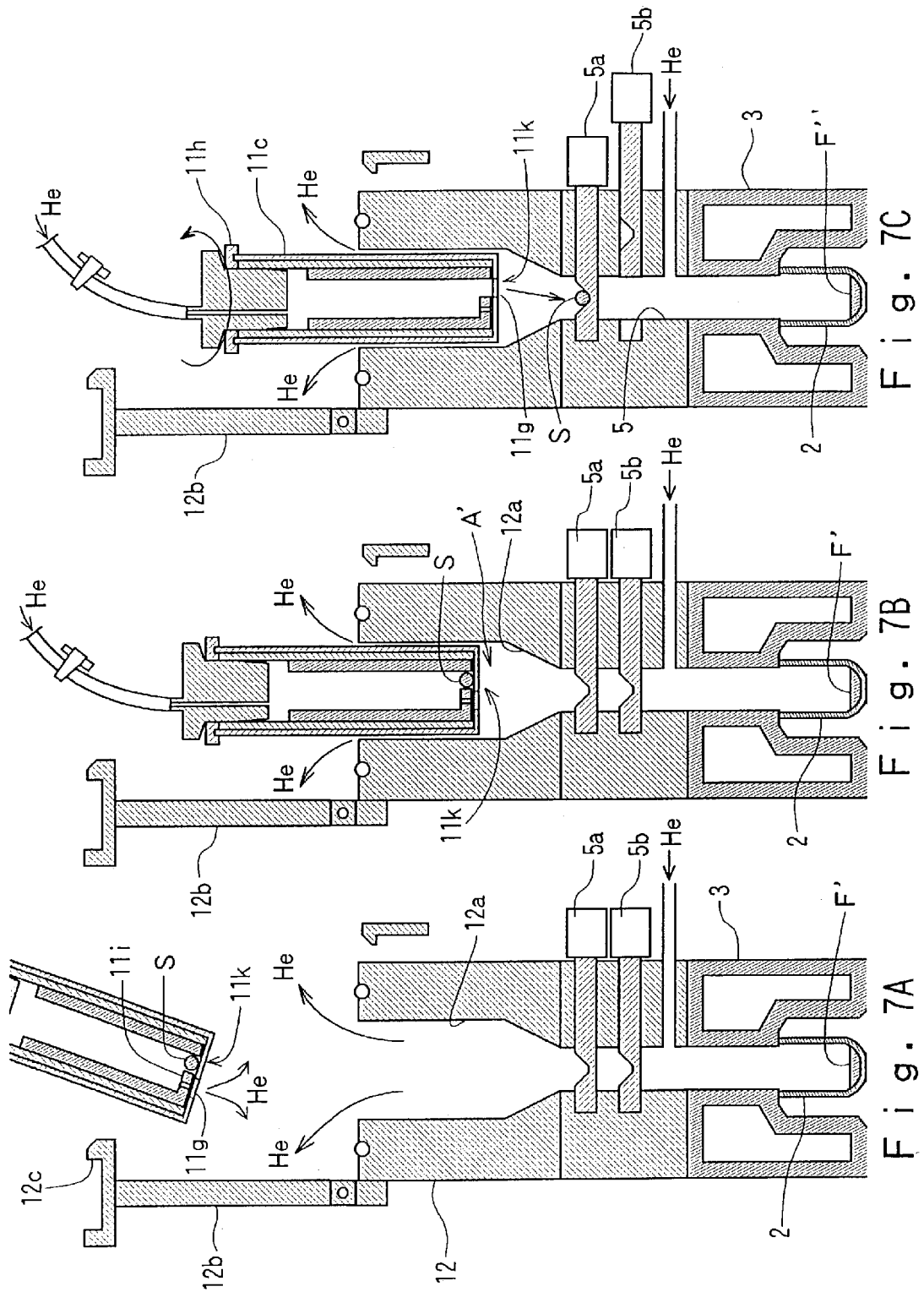
FIG. 7 is a view for describing a motion of the contained oxygen analyzing apparatus.

FIGS. 5 to 7 is a view showing a second embodiment in accordance with the present invention, in which FIG. 5A shows a structure of a preliminary reducing furnace 10 corresponding to the preliminary reducing furnace 4 mentioned above, FIG. 5B shows a structure of a main body 1' of the contained oxygen analyzing apparatus 1, and FIGS. 7A to 7C are views describing a method of inputting the sample S to be measured into the oxygen analyzing apparatus main body 1'. In the embodiment shown in FIGS. 5 to 7, since parts having the same reference symbols as those in FIGS. 1 to 14 are the same or corresponding parts, a detailed description thereof will be omitted.

As shown in FIG. 5A, the preliminary reducing furnace 10 in accordance with the present embodiment is provided independently from the oxygen analyzing apparatus main body 1', and is structured such as to heat the sample S to be measured by inserting a sample holding body 11 into an inner portion thereof, thereby reducing the oxide film formed on a surface thereof.

The preliminary reducing furnace 10 has, for example, a guide tube 10a capable of inserting the sample holding body 11 to an inner portion thereof, a heater 10b wound around an outer periphery of the guide tube 10a, and a power source 10c supplying an electric power to the heater 10b.

On the other hand, the sample holding body 11 has, for example, a preliminary reducing crucible 11a heating the sample S to be measured in a state of positioning the sample S to be measured in an inner portion thereof, a tube body 11b brought into contact with an outer periphery of the preliminary reducing crucible 11a, thereby holding the preliminary reducing crucible 11a in an inner portion thereof, a closed-end tube body 11c rotatably mounted so as to cover the tube body 11b, a lid body 11e forming a door for closing one end side of the tube body 11b and an inflow port lid for the helium gas (He) corresponding to the inert gas, and a flow rate regulating valve 11f for the helium gas (He).

Further, a discharge port 11g for the helium gas (He) is formed at a position deflecting from a center thereof, in another end side of the tube body 11c, and a flange 11h for rotating the tube body 11c is formed in one end side. On the other hand, a step portion 11h protruding to an inner portion at a position closing the discharge port 11g and used for holding the sample S to be measured in the inner portion is formed in another end side of the preliminary reducing crucible 11a, and a discharge port 11j for discharging some of the helium gas (He) is formed in the step portion 11h.

Further, the bottom surface of the tube body 11c is structured such as to form a lid body 11k opening and closing another end side of the sample holding body 11 in correspondence to the rotation of the tube body 11c.

Accordingly, when applying the electric current to the heater 10b while circulating the helium gas (He) in a state of inserting another end side of the sample holding body 11 into the guide tube 10a, it is possible to heat the sample S to be measured while purging the inner side of the sample holding body 11 by the helium gas (He), and it is possible to reduce the oxide film of the sample S to be measured while keeping a state of being isolated from the ambient air.

On the other hand, as shown in FIG. 5B, the analyzing apparatus main body 1' forms a hopper 12 to which the sample S to be measured within the sample holding body 11 can be input while keeping the state of being isolated from the ambient air.

The structure of the hopper 12 has an opening portion 12a which communicates, for example, with the analyzing furnace 3 and can keep a state of being isolated from the ambient air by circulating helium gas (He) corresponding to one example of the inert gas to an inner portion thereof, a lid body 12b which opens and closes an open end portion of the opening portion 12a, a hook 12c for holding a closed state of the lid body 12b, and a seal 12d (an O-ring) for keeping the opening portion 12a in an air-proof state from an external portion in a state of closing the lid body 12b.

Accordingly, it is possible to input the metal flux F and input the sample S to be measured via the same opening portion 12a, and it is possible to keep the inner portion of the opening portion 12a in the state of being isolated from the ambient air by purging the helium gas (He). Further, since it is possible to restrict an amount of consumption of the helium gas (He) by closing the lid body 12b, it is possible to restrict a running cost.

In this case, in accordance with the present embodiment, since the structure is made such that both of the metal flux F and the sample S to be measured can be input via the same opening portion 12a, it is desirable to slide the sample holder 5a as illustrated at a time of making the sample holder 5b hold the metal flux F, thereby opening the communication passage 5. In the same manner, at a time of inputting the sample S to be measured held by the sample holder 5a into the graphite crucible 2, it is desirable to slide the sample holder 5b as shown in FIG. 7C so as to open the communication passage 5. Further, it is possible to consider a modification that a sample holder is formed by combining the sample holder 5a and the sample holder 5b as one unit.

FIG. 6 shows a modified embodiment of the hopper 12 shown in FIG. 5B. Reference symbol 12e denotes a lid body which slides in a horizontal direction with respect to the opening portion 12a. It is possible to make a volumetric capacity of the opening portion 12a small by making the structure as the present embodiment. That is, the structure of the lid body may be such as to close the opening portion 12a by rotating so as to press the opening portion 12a from the above, or open and close by sliding laterally. However, it is possible to reduce the volumetric capacity of the opening portion 12a so as to make the amount of consumption of the inert gas (He) consumed in correspondence to the opening and closing motion of the lid body 12e further small, by sliding the lid body 12e in a lateral direction.

Next, a description will be given of an operation at a time of inputting the sample S to be measured after being preliminarily reduced within the preliminary reducing furnace 10 via the opening portion 12a, by using the hopper 12. In this case, in the following FIG. 7, there is shown an example of the hopper 12 forming the lid body 12b which opens and closes mainly in correspondence to rotation in the vertical direction; however, it is possible to input the sample S to be measured in accordance with approximately the same way in the hopper 12 forming the lid body 12e which opens and closes on the basis of a sliding motion.

First, as shown in FIG. 7A, the lid body 12b is opened so as to make it possible to insert the sample holding body 11. At this time, the helium gas (He) goes on flowing out from both of the opening portion 12a and the discharge port 11g, and the sample S to be measured maintains a state of being isolated from the ambient air within the sample holding body 11. Further, the sample S to be measured is moved to a position deflecting from the step portion 11i by slightly tilting the sample holding body 11. In this case, in order to make it easy to insert the sample holding body 11, it is desirable to form an outer diameter somewhat smaller than an inner diameter of the opening portion 12a.

Next, as shown in FIG. 7B, the sample holding body ii is inserted into the opening portion 12a. Since the helium gas (He) supplied to both of the sample holding body 11 and the hopper 12 is discharged to the external portion through a gap formed between an inner periphery of the opening portion 12a and an outer periphery of the sample holding body 11 at this time, a flow rate thereof is increased, so that no ambient air flows against this flow. That is, a space A' within the opening portion 12a securely becomes in the state of being isolated from the ambient air. In this case, when the outer diameter of the sample holding body 11 is made too small in comparison with the inner diameter of the opening portion 12a, the gap becomes wide, so that it is necessary to discharge a sufficient flow rate of helium gas (He) so as to prevent the ambient air from entering thereinto.

Further, a position of the discharge port 11g is aligned with a position of the sample S to be measured by carrying out a rotating operation of the flange 11h from one end side of the sample holding body 11 as shown in FIG. 7C, whereby it is possible to open the lid body 11k and it is possible to move the sample S to be measured to the sample holder 5a in a state of being isolated from ambient air. That is, it is possible to keep a state of being completely isolated from ambient air due to the flow of the inert gas (He), also at a time of moving the sample S to be measured by using the sample holding body 11.

In accordance with the structure of the present embodiment, it is possible to obtain the same effect as that of first embodiment shown in FIGS. 1 to 4, and it is possible to make the structure in the side of the main body 1' of the contained oxygen analyzing apparatus 1 simple, by forming the preliminary reducing furnace 10 as an independent body. Further, the structure can be achieved only by mounting the hopper 12 to the existing contained oxygen analyzing apparatus 1. In this case, the measuring procedure is the same as the first embodiment.

Further, since the detailed structure described above is exemplified so as to easily describe the present invention, it goes without saying that the detailed structure mentioned above does not limit the contents of the present invention.

Figure 8:
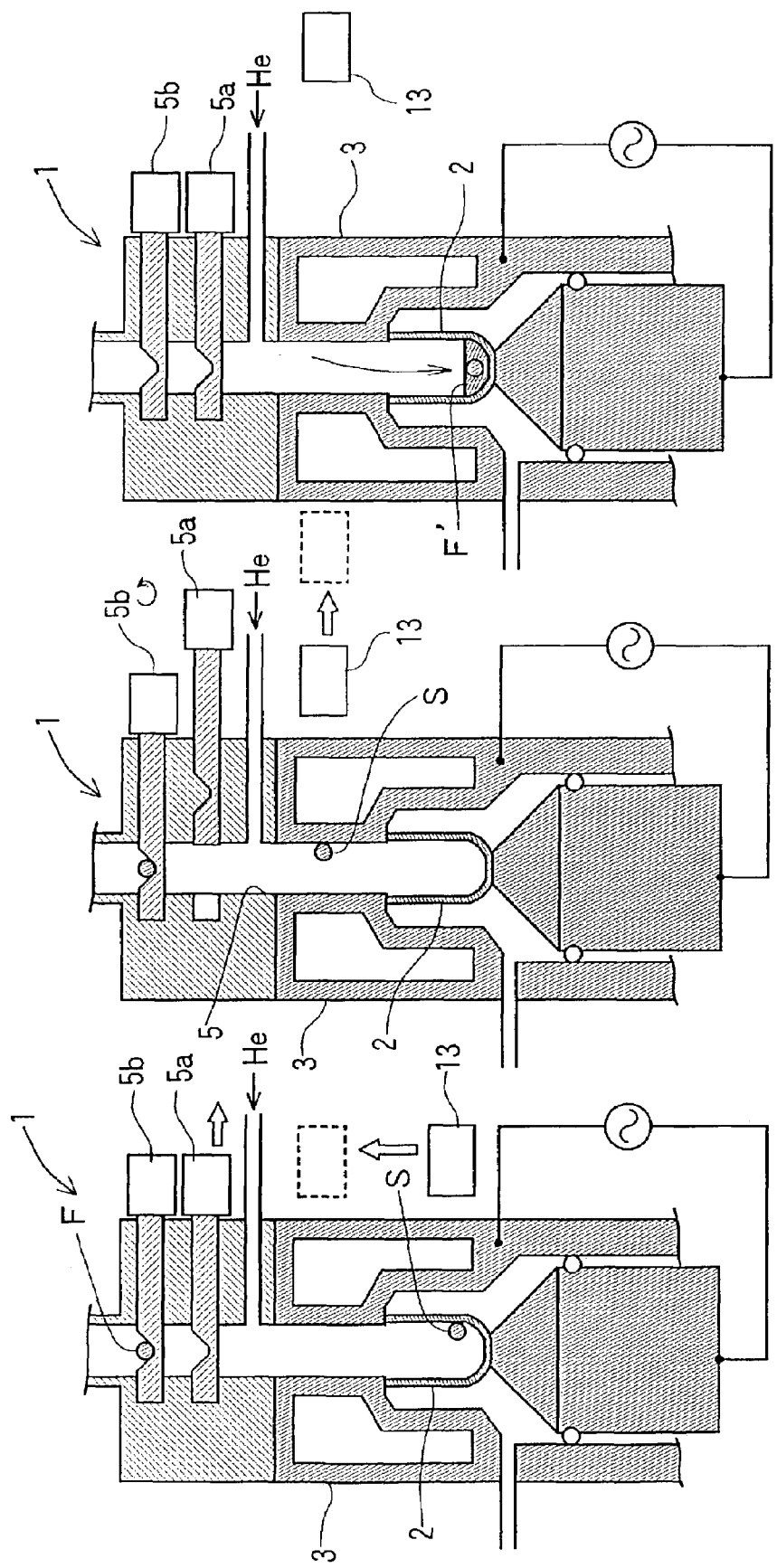
FIG. 8 is a view describing a structure and a motion of a contained oxygen analyzing apparatus in accordance with a third embodiment.
Figure 9:
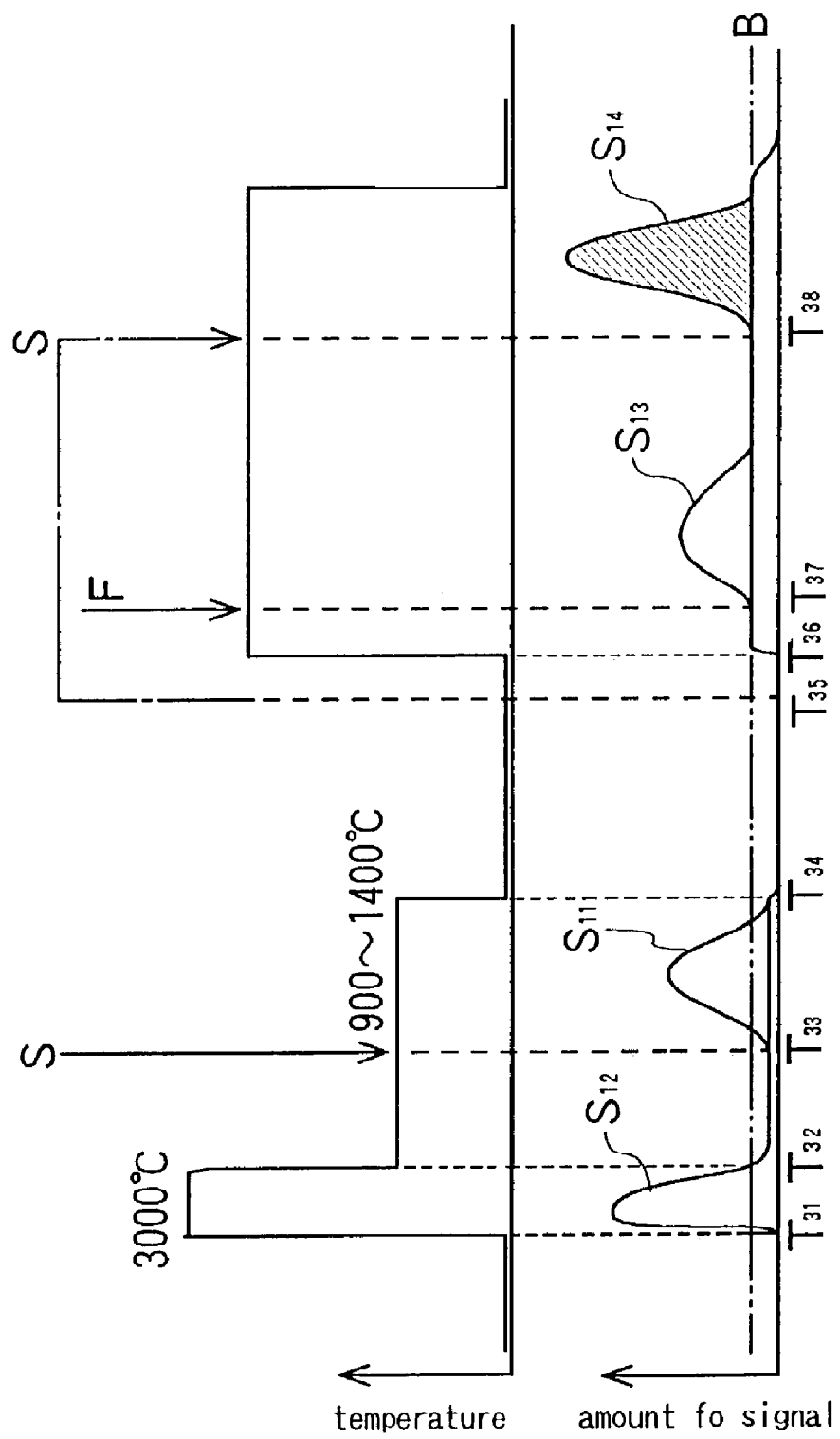
FIG. 9 is a view for describing a motion of the contained oxygen analyzing apparatus.

FIGS. 8 and 9 are views showing a third embodiment in accordance with the present invention, in which FIGS. 8A to 8C are views showing a structure and a motion of the contained oxygen analyzing apparatus 1 in accordance with the present embodiment, and FIG. 9 is a view showing a relation between a temperature within the analyzing furnace 3 and an amount of generated gas (an amount of signal in the analyzer 7). In FIGS. 8 and 9, since parts having the same reference symbols as those in FIGS. 1 to 7 are the same parts or corresponding parts, a detailed description thereof will be omitted.

In this case, a position of the sample holder 5a which holds the sample S to be measured so as to input into the graphite crucible 2, and a position of the sample holder 5b which holds the metal flux F so as to input into the graphite crucible 2 in the present embodiment are arranged so as to be inverse to those shown in FIGS. 2 and 4.

In the contained oxygen analyzing apparatus 1 in accordance with the present embodiment, a magnet 13 is arranged on a side surface of the graphite crucible 2, and the magnet 13 can be moved to at least three positions respectively shown in FIGS. 8A to 8C in accordance with a control from a control portion (not shown) of the contained oxygen analyzing apparatus 1. Further, the sample S to be measured by the contained oxygen analyzing apparatus 1 in accordance with the present invention is a magnetic body (desirably, a ferromagnetic body) such as steel or the like, and the metal flux F is a non-magnetic body (a material which is not a ferromagnetic body). That is, the magnet 13 corresponds to one example of a sample take-out unit for temporarily taking out the sample S to be measured within the graphite crucible 2 in the state of being isolated from the ambient air and holding the sample S to be measured.

As shown in FIG. 9, in the contained oxygen analyzing apparatus 1 in accordance with the present embodiment, first, between time points $T_{31}$ and $T_{32}$, the graphite crucible 2 is heated to about 3000° C., is degasified and thereafter the analyzing furnace 3 is left until the inside temperature is decreased to be equal to or less than a boiling point of the steel 1540° C. Further, at a time point $T_{33}$, the oxide film on the surface of the steel S is reduced by inputting the steel S into the graphite crucible 2 and controlling the temperature within the analyzing furnace 3 between 900° C. and 1400° C.

Next, when the reduction of the oxygen film of the steel S is finished, the heating of the analyzing furnace 3 is stopped at a time point $T_{34}$, the steel S is left until the temperature thereof is cooled down to be equal to or less than the Curie temperature (780° C.). Then, at a time point $T_{35}$, the steel S is moved on the basis of the magnetic force by arranging the magnet 13 at a position shown in FIG. 8A, and the steel S is moved from the outer portion of the analyzing furnace 3 to a portion which is not affected by the heat of the carbon furnace 2, by moving the magnet 13 upward, as shown in FIG. 8B. That is, the magnet h3 in accordance with the present embodiment structures a magnetic force induction portion which can take out the steel S from the inner side of the graphite crucible 2 by using the attractive force caused by the magnetic force.

After moving the steel S, the temperature within the analyzing furnace 3 is heated to an analyzing temperature (2400° C.) at a time point $T_{36}$, and at a time point $T_{37}$, the communication passage 5 is opened by sliding the sample holder 5a as shown in FIG. 8B, and the powder or granular metal flux F is input into the graphite crucible 2 by rotating the sample holder 5b. Accordingly, the flux F forms a metal flux F', the oxygen therein is discharged, and this is stored as the base line B in a state that the amount of gas generated from the graphite crucible 2 is stable.

Further, at a time point $T_{38}$, the steel sample S is released from the influence of the magnetic force by moving the magnet 13 away from the analyzing furnace 3 as shown in FIG. 8C, thereby inserting the sample into the graphite crucible 2. Accordingly, it is possible to accurately measure the contained oxygen in the inner portion of the steel S on the basis of a signal $S_{14}$.

In accordance with the structure of the present embodiment, it is possible to completely remove the oxide film formed on the surface of the sample S to be measured within only one graphite crucible 2, and it is possible to accurately analyze the amount of oxygen contained in the metal flux F by heating and dissolving the metal flux F within the same graphite crucible 2 so as to degasify the metal flux F, heating again the sample S to be measured in the state in which the base line B is stable, and dissolving this. That is, the contained oxygen analyzing apparatus 1 can carry out an accurate analysis using the metal flux F while the structure thereof is extremely simple, and it is possible to reduce a manufacturing cost thereof.

Further, since the sample S to be measured after the oxide film is reduced can be analyzed without being taken out from the contained oxygen analyzing apparatus 1, it is possible to securely keep a state of being isolated from the ambient air, and it is possible to securely prevent the reformation of the oxide film. Further, since it is not necessary to repeat a process of removing the oxide film of the sample S to be measured as in the conventional embodiment shown in FIG. 14 again and again, it is possible to rapidly analyze a sample.

In this case, in the embodiment mentioned above, there is shown a permanent magnet as the magnet 13; however, an electromagnet may be used in place thereof, and in this case, since it is possible to electrically regulate a strength of the magnetic force applied to the sample S to be measured, it is possible to reduce the movement of the magnet. Further, as the embodiment shown in FIG. 2, it is possible to effectively apply a weak magnetic force by using a rod body 8c.

In addition, in the case that the sample S to be measured is not a magnetic body, the sample take-out means may be formed as a scooping up structure using a suction, a rod body or the like.

Figure 10:
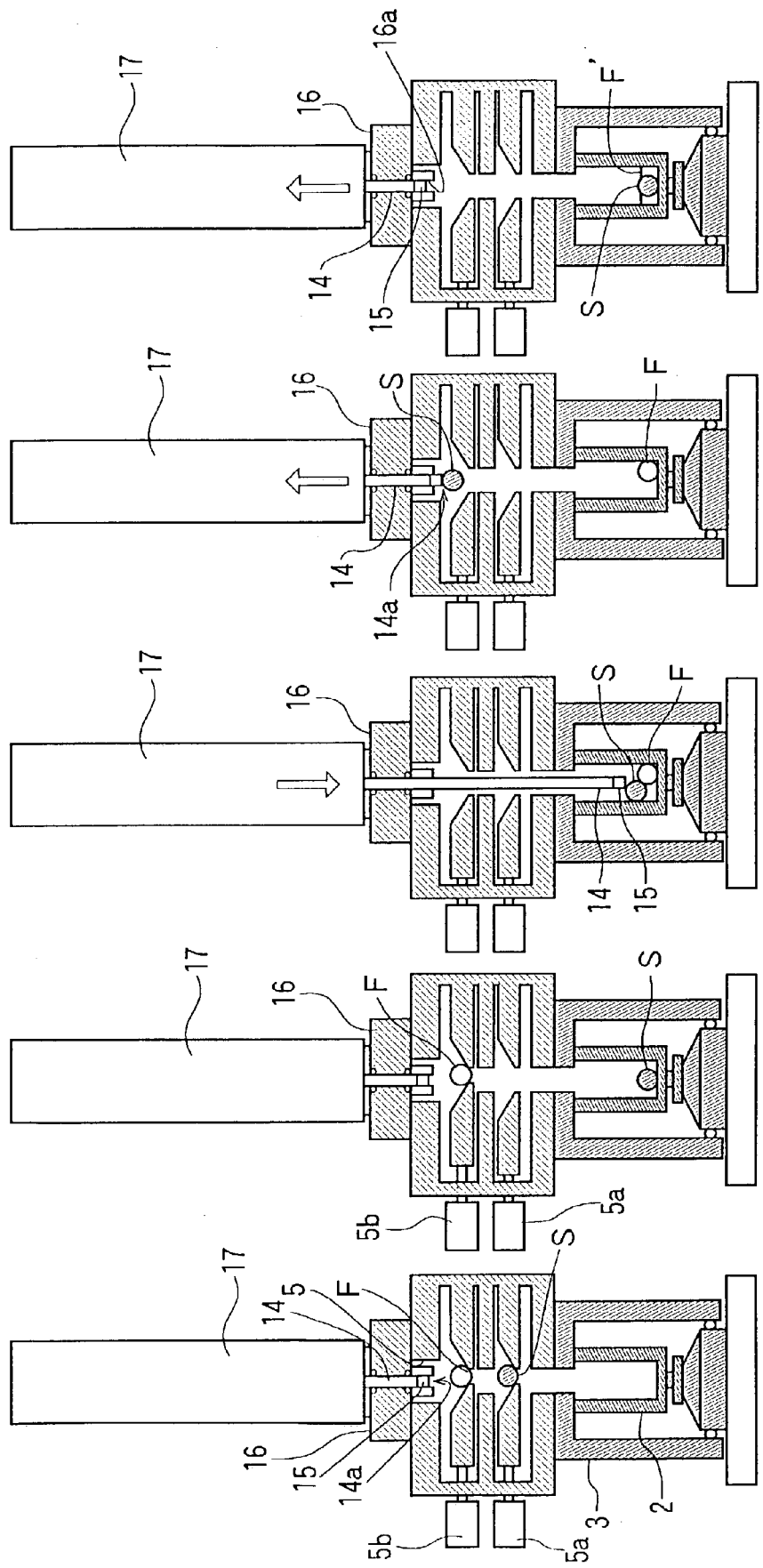
FIG. 10 is a view showing a modified embodiment of the contained oxygen analyzing apparatus shown in FIG. 8.
Figure 11:
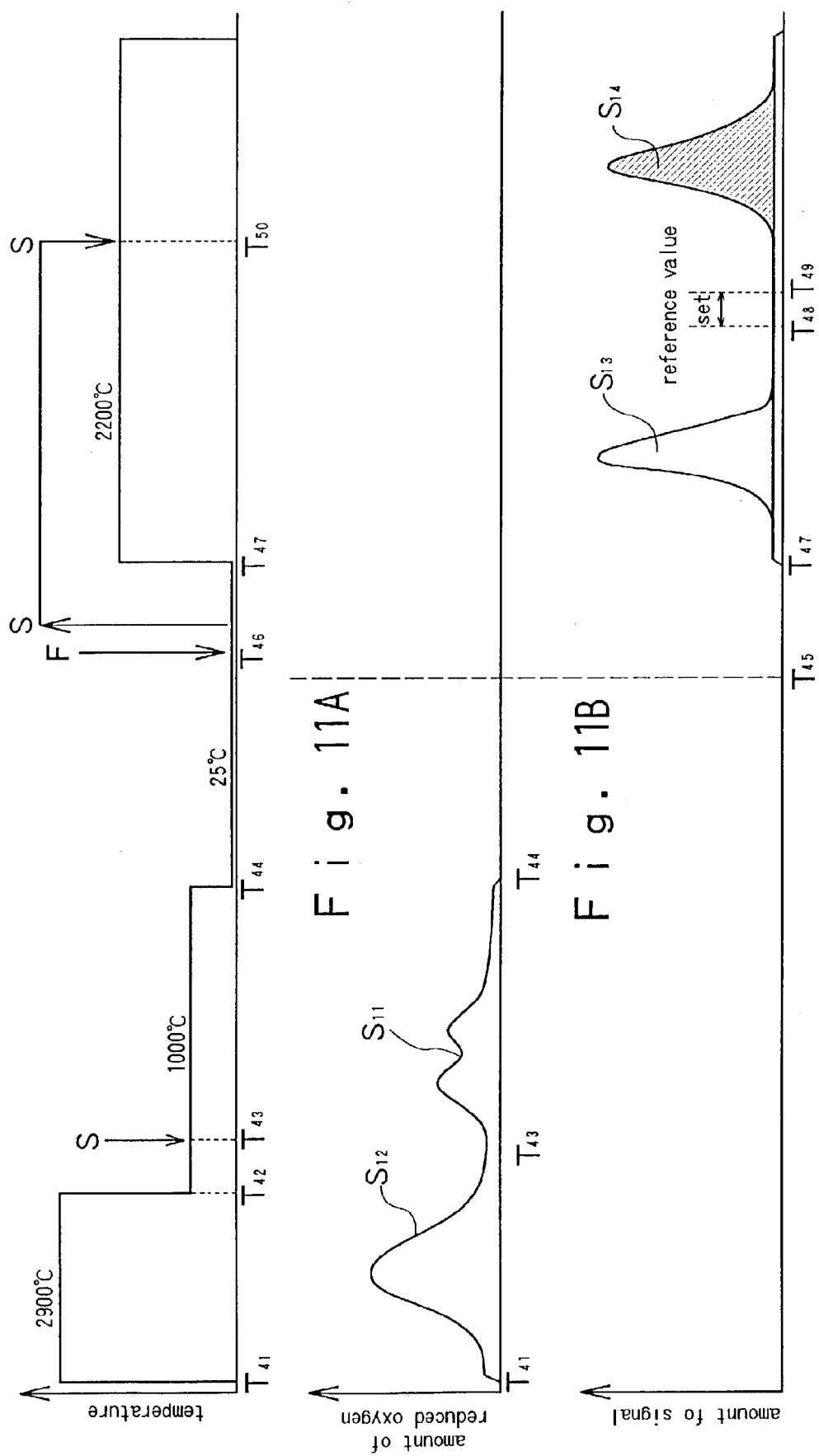
FIG. 11 is a view for describing a motion of the contained oxygen analyzing apparatus.

FIGS. 10 and 11 are views showing a fourth embodiment in accordance with the present invention. The fourth embodiment corresponds to an embodiment obtained by modifying the contained oxygen analyzing apparatus in accordance with the third embodiment shown in FIGS. 8 and 9. Further, FIGS. 10A to 10E are views showing a structure and a motion of the contained oxygen analyzing apparatus 1 in accordance with the present embodiment, and FIGS. 11A to 11C are views showing a relation between the temperature within the analyzing furnace 3 and the amount of the generated gas (the amount of signals of the analyzer 7). FIG. 11A shows a temperature change of the graphite crucible 2 and FIGS. 11B and 11C show an amount of oxygen reduced by heating.

In this case, also in FIGS. 10 and 11, since parts having the same reference symbols as those in FIGS. 1 to 9 are the same or the corresponding portions, a detailed description will be omitted. Further, the sample S to be measured in the present embodiment is the magnetic body, for example, the steel. On the other hand, the metal flux F is the non-magnetic body, for example, tin.

In FIG. 10, reference numeral 14 denotes a rod body corresponding to one example of the sample take-out unit for temporarily taking out and holding the sample S to be measured in a state of being isolated from ambient air, reference numeral 15 denotes a magnetic force application portion formed by a permanent magnet (a ferromagnetic body) mounted to a leading end portion 14a of the rod body 14, reference numeral 16 denotes a lid body formed so as to be capable of closing the communication passage 5, and reference numeral 17 denotes an actuator sliding the rod body 14 in a vertical direction. Further, the rod body 14 mentioned above extends through the lid body 16 so as to freely move forward and backward (vertically move) with respect to the lid body 16 and to be airtight with respect to ambient air.

In this case, although an illustration is omitted also in the contained oxygen analyzing apparatus 1 in accordance with the present embodiment, the flow passage switching valve 7a (refer to FIG. 2) is formed between the analyzing furnace 3 and the analyzer 7. That is, the preliminary reduction of the sample to be measured and the degasification of the graphite crucible 2 can be controlled by switching a flow passage switching valve so that the oxide gas does not flow through the analyzer 7.

Next, a description will be given of an operation of the contained oxygen analyzing apparatus 1 in accordance with the present embodiment. First, as shown in FIG. 11A, the graphite crucible 2 is heated to about 2900° C. in a state shown in FIG. 10A, first at time points $T_{41}$ to $T_{42}$. At this time, as shown by reference numeral S12 in FIG. 11B, a degasification for the graphite crucible 2 is applied. However, the gas flow passage for the carbon monoxide (CO) or the like generated due to the reduction is switched by the flow passage switching valve 7a or the like so as to prevent the gas from flowing into the analyzer 7. Thereafter, the temperature is regulated, for example, to about 1000° C.

Next, at a time point $T_{43}$, as shown in FIG. 10B, when the steel S is input into the graphite crucible 2 by sliding the sample holder 5a, the oxide film on the surface of the steel S is reduced and gas such as carbon monoxide (CO) or the like is discharged, as shown by reference numeral $S_{11}$. Then, at a time point $T_{44}$ when a sufficient time has passed, the heating of the graphite crucible 2 is stopped, and the temperature within the graphite crucible 2 is cooled to about room temperature 25° C.

In this case, the graphite crucible 2 can be quickly cooled by circulating a cooling water within the internal space 3f of the upper electrode 3a shown in FIG. 2. Next, at a time point $T_{45}$, the gas flow passage is switched so that the analyzing furnace 3 in communication with the analyzer 7.

Further, at a time point $T_{46}$, the metal flux F is input into the graphite crucible 2 by sliding the sample holder 5b, and the rod body 14 is dropped into the graphite crucible 2 by using the actuator 17 mentioned above. At this time, the temperature of the steel S is cooled down to be equal to or less than the Curie temperature (780° C.), and both the metal flux F and the steel S are received within the graphite crucible 2; however, only the magnetic body, the steel S is attracted by the magnetic force of the permanent magnet 15 mounted to the leading end portion 14a of the rod body 14.

Accordingly, as shown in FIG. 10D, when the actuator 17 lifts up the rod body 14, it is possible to adhere only the steel S to the leading end portion 14a thereof so as to take out only the steel S from the inner side of the graphite crucible 2. Further, the magnetic force of the permanent magnet 15 is set to a magnitude sufficient to selectively lift up the steel S within the graphite crucible 2, it is not necessary to charge a strong magnetism without discretion and it is possible to have almost no influence to the periphery.

In addition, in accordance with the present embodiment, the structure is made simple by using a permanent magnet corresponding to the ferromagnetic body as the magnetic force application portion 15; however, the magnetic force application portion 15 formed in the leading end portion 14a of the rod body 14 is not limited to a permanent magnet, but may be formed by an electromagnet mounted to a base end portion of the rod body 14 corresponding to the magnetic body. In this case, a magnitude of an adhering force applied to the steel S can be regulated by a magnitude of electric power supplied to the electromagnet.

When lifting up the steel S from the inner side of the graphite crucible 2, at the next time point $T_{47}$, the graphite crucible 2 is again heated and the temperature thereof is regulated so as to be between 2200° C. and 2400° C. At this time, the metal flux F is dissolved, and the oxygen contained therein is reduced, whereby the oxide gas shown by a curve S13 is detected by the detector 7. Further, when the metal flux F is dissolved so as to form the metal flux F' and the oxygen contained therein is reduced, the concentration of the oxide gas becomes stable.

When the concentration of the oxide gas detected by the detector 7 becomes stable, the reference value B is next set between time points $T_{48}$ and $T_{49}$. Further, at a time point $T_{50}$, the steel S is again input into the graphite crucible 2 as shown in FIG. 10E. At this time, the actuator 17 further retracts the rod body 14 into a through hole 16a (refer to FIG. 10) for the rod body 14 formed in the lid body 16 by further lifting up the rod body 14, thereby making the force applied to the steel S from the permanent magnet 15 smaller than the force of gravity and inputting the steel S into the graphite crucible 2.

However, in the case of forming the magnetic force application portion 15 by an electromagnet, it is possible to input the steel S into the graphite crucible 2 by stopping the electric power supplied to the electromagnet.

In accordance with the structure mentioned above, since it is not necessary to strengthen the magnetic force generated from the magnetic force application portion 15 formed in the leading end portion 14a of the rod body 14, and it is possible to attract the steel S securely, it is possible to simplify the structure of the sample take-out unit. That is, it is possible to reduce the manufacturing cost and create an energy saving, and there is no risk that the motion of the peripheral equipment is affected. In addition, since it is sufficient to take out the steel from the inner side of the graphite crucible in accordance with the attraction magnetic force only by vertically sliding the rod body, it is possible to easily achieve automation.

However, in the case that the sample S to be measured is not a magnetic body, it is desirable to make the structure of the sample take-out unit a structure similar to an endoscope for medical use.

Figure 12:
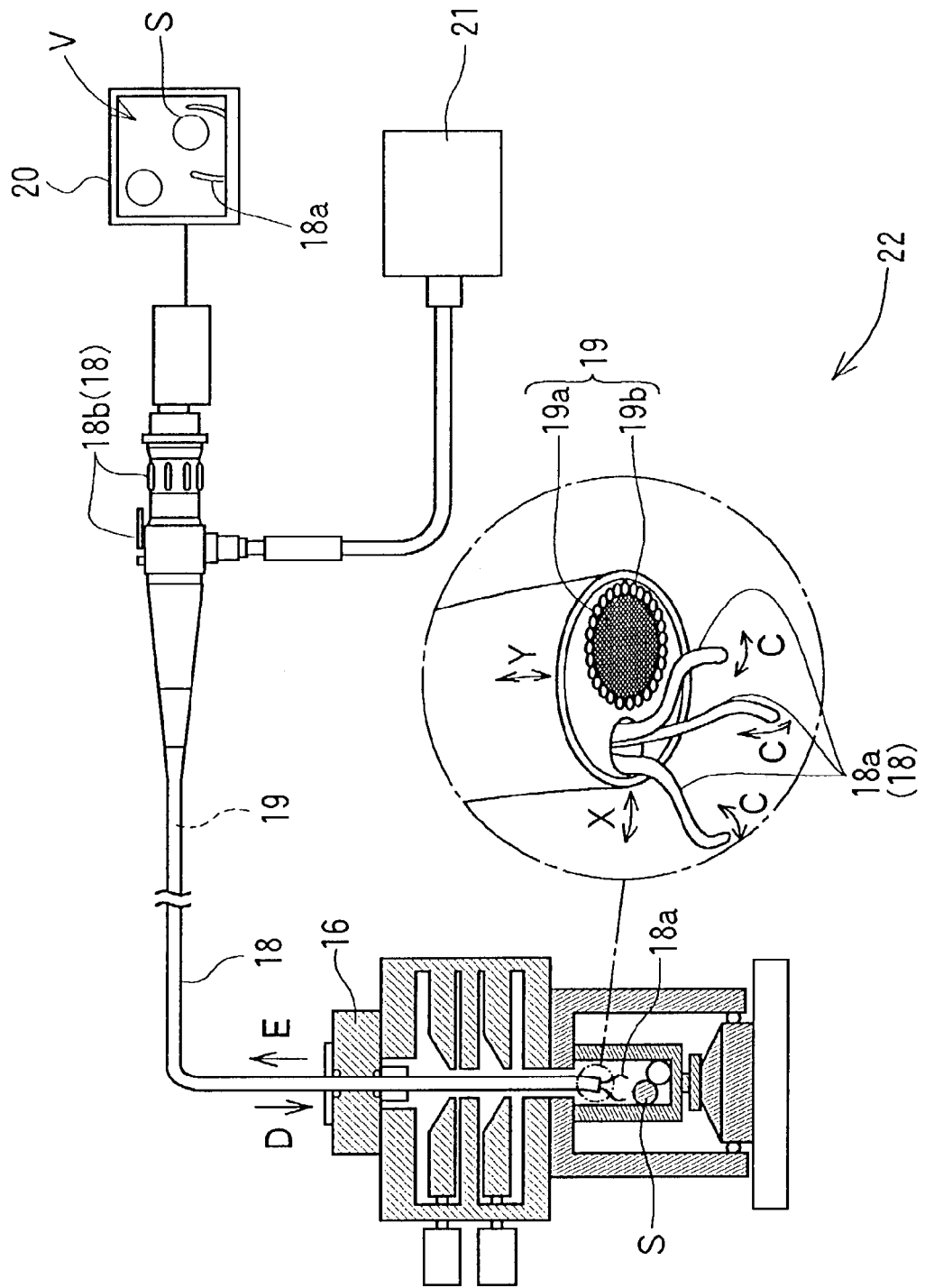
FIG. 12 is a view showing a further modified embodiment of the contained oxygen. analyzing apparatus.
Figure 13A:
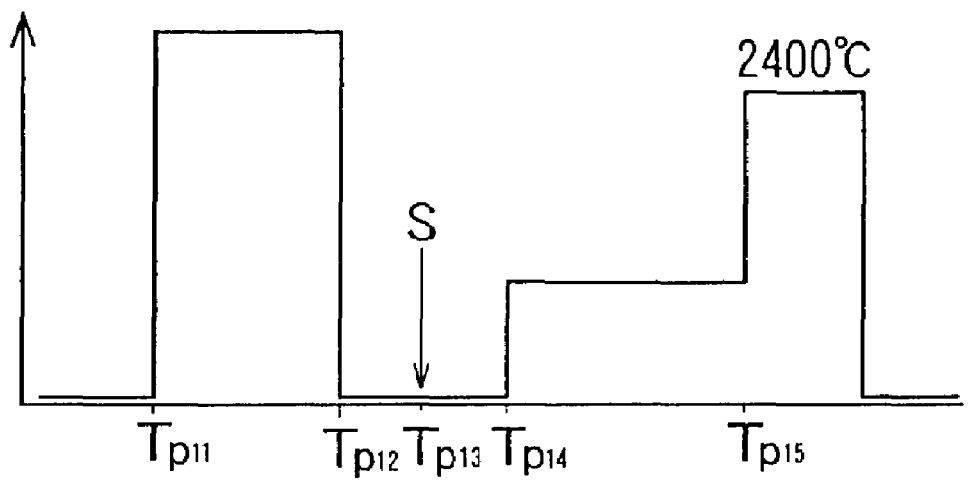
FIG. 13 is a view describing one example of a motion of a conventional contained oxygen analyzing apparatus.
Figure 13B:
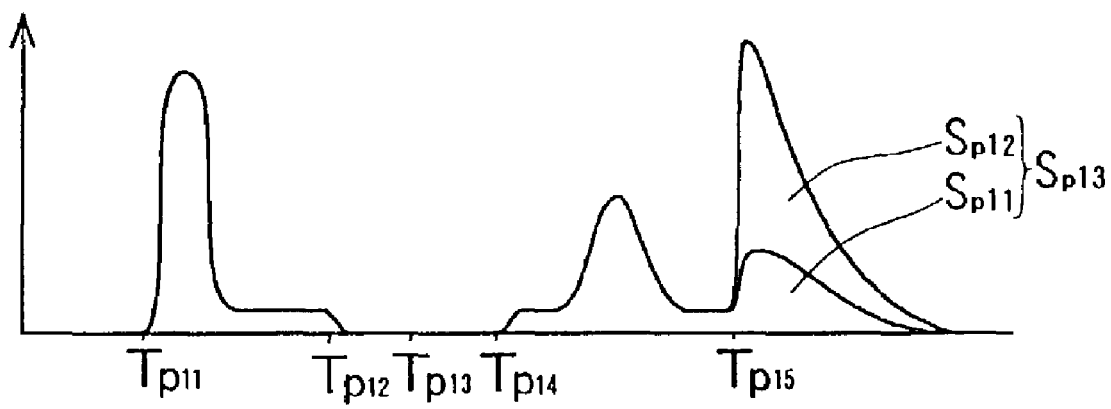

FIG. 12 is a view showing a fifth embodiment in accordance with the present invention. The contained oxygen analyzing apparatus 1 shown in FIG. 12 corresponds to a further modified embodiment of the sample take-out unit 13 and 14 shown in FIGS. 8 and 10, and since parts having the same reference symbols as those in FIGS. 1 to 11 are the same of the corresponding members, a detailed description thereof will be omitted.

In FIG. 12, reference numeral 18 denotes a gripping means having a clamp 18a for gripping the sample S to be measured in a leading end portion and having an operation portion 18b for carrying out a tilting motion of the clamp 18a in a two-dimensional direction X and Y and a gripping operation (in a direction of an arrow C) of the clamp 18a, reference numeral 19 denotes a fiber scope which is arranged so as to be along the gripping means 18 and is used for checking a state near a leading end portion thereof by means of an image V, reference numeral 20 denotes a display portion which displays the image V transmitted by a pixel fiber 19a of the fiber scope 19, and reference numeral 21 denotes a light source which irradiates a light to the inner side of the graphite crucible 2 by using a floodlight fiber 19b of the fiber scope 19. That is, a take-out unit 22 in the present embodiment is constituted by the gripping means 18, the fiber scope 19, the display portion 20 and the light source 21.

The contained oxygen analyzing apparatus 1 in accordance with the present invention analyzes approximately in the same manner as that of the fourth embodiment shown in FIGS. 10 and 11. Then, at a time of taking out the sample S to be measured in the time point $T_{46}$ in FIG. 11, the gripping means is dropped down within the graphite crucible 2 as shown by an arrow D. At this time, an operator can real-time check the condition near the leading end portion of the gripping means 18 by using the image V displayed on the display portion 20, and can operate the operation portion 18b while seeing the image V.

That is, since the operator can operate the operation portion 18b while seeing the display portion 20 so as to pick up the sample S to be measured by the clamp 18a, it is possible to securely pick up the sample S to be measured whatever the sample S to be measure is made of, thereby taking out the sample from the graphite crucible 2 as shown by an arrow E. Further, it is possible to easily input the sample S to be measured in accordance with the operation of the operation portion 18b at a time point $T_{50}$.

In this case, the contained oxygen analyzing apparatus 1 in accordance with the present invention is not limited to the gripping means 18, the fiber scope 19, the display portion 20 and the light source 21 in the detailed structure. Further, in the present embodiment, there is shown an embodiment which the operator manually operates; however, the structure may be made such that each of the operations shown by the arrows C to E, X and Y mentioned above is electrically controlled from a side of the main body of the contained oxygen analyzing apparatus 1 by making it possible to control electrically the operation portion 8b or the like.

In each of the embodiments mentioned above, there is shown an embodiment in which the metal flux F is used for heating and dissolving the sample S to be measured, whereby it is possible to securely dissolve the heat resisting oxide even in the case that the oxygen concentration in the sample S to be measured is high; however, the present invention is not limited to using the metal flux F. Further, there is shown an embodiment using helium gas (He) as the example of the inert gas; however, it goes without saying that an argon gas (Ar) or other inert gases can be used in place of helium gas (He).

In accordance with the contained oxygen analyzing apparatus and the contained oxygen analyzing method of the present invention, it is possible to quantitatively analyze the trace quantity of contained oxygen existing within the sample to be measured with a high accuracy, without being affected by the oxide film generated on the surface of the sample to be measured, while being a simple structure.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. In a contained oxygen analyzing apparatus, which analyzes and outputs an amount of contained oxygen in a sample to be measured by inputting the sample into an analyzing crucible within an analyzing furnace and heating and dissolving the sample, the improvement comprising:
    a preliminary reducing furnace unit having a preliminary reducing crucible and a power source for preliminarily reducing an oxide film on a surface of the sample by heating the sample to a temperature equal to or less than a melting point in a state of being apart from ambient air, the preliminary reducing furnace having a discharge hole for discharging gases formed in the preliminary reducing furnace;
    a gas used for the reduction; and
    a sample inputting unit for inputting the reduced sample to be measured from the preliminary reducing furnace unit into an analyzing crucible via a communication passage, the communication passage configured so that the preliminary reducing furnace and the analyzing crucible communicate in a state where the sample is isolated from ambient air.

2. The contained oxygen analyzing apparatus of claim 1, wherein the preliminary reducing furnace unit is counnected to an upper portion of the analyzing crucible, and includes a step portion for retaining the sample within the analyzing crucible by inhibiting the sample from moving in the horizontal direction.

3. The contained oxygen analyzing apparatus of claim 1, wherein the preliminary reducing furnace unit includes an approximately tubular preliminary reducing crucible and a heater coil is wrapped around the tubular preliminary reducing crucible.

4. The contained oxygen analyzing apparatus of claim 3 wherein the tubular preliminary reducing crucible is connected to a source of reducing gas and has a discharge hole for releasing the reducing gas.

5. The contained oxygen analyzing apparatus of claim 3 wherein the sample inputting unit includes a piston for forcing the sample to be removed from the tubular preliminary reducing crucible.

6. The contained oxygen analyzing apparatus of claim 3 wherein the sample inputting unit includes a movable rod applying a magnetic attracting force to the sample to remove the sample from the tubular preliminary reducing crucible.

7. The contained oxygen analyzing apparatus of claim 6 further including a slide drive portion for moving the movable rod.

8. The contained oxygen analyzing apparatus of claim 6 further including an electromagnetic member operatively attached to the movable rod to provide the magnetic attracting force.

9. The contained oxygen analyzing apparatus of claim 1, wherein the sample inputting unit further comprises an actuator which introduces the sample into the analyzing furnace by moving the sample in the horizontal direction over the step portion.

10. The contained oxygen analyzing apparatus of claim 9, further including means for the heated coil to be turned off to permit the sample to be cooled prior to being inputted into the analyzing furnace.

11. The contained oxygen analyzing apparatus of claim 9 wherein the preliminary reducing crucible is provided with hydrogen gas at a pressure level above an ambient air pressure.

12. In a contained oxygen analyzing apparatus, which analyzes and outputs an amount of contained oxygen in a sample to be measured by inputting the sample into an analyzing crucible within an analyzing furnace and heating and dissolving the sample, the improvement comprising:

means for preliminarily reducing an oxide film on a surface of the sample by heating the sample to a temperature equal to or less than a melting point in a state of being apart from ambient air including a preliminary reducing furnace having a discharge hole for discharging gases formed in the preliminary reducing furnace;

a gas used for the reduction connected to the preliminary reducing furnace; and means for inputting the reduced sample to be measured from the preliminary reducing furnace unit into an analyzing crucible via a communication passage, the communication passage configured so that the preliminary reducing furnace and the analyzing crucible communicate in a state where the sample is isolated from ambient air.

13. The contained oxygen analyzing apparatus of claim 12, wherein the preliminary reducing furnace unit is connected to an upper portion of the analyzing crucible, and includes a step portion for retaining the sample within the analyzing crucible by inhibiting the sample from moving in a horizontal direction.

14. The contained oxygen analyzing apparatus of claim 12 further including means for lowering the temperature of the reduced sample to a temperature above ambient before the reduced sample is removed from the preliminary reducing furnace unit.

* * * * *